United States Patent [19]

Kalish

[11] Patent Number: 5,527,829
[45] Date of Patent: Jun. 18, 1996

[54] HIV PROTEASE INHIBITORS

[75] Inventor: Vincent J. Kalish, San Diego, Calif.

[73] Assignee: Agouron Pharmaceuticals, Inc., San Diego, Calif.

[21] Appl. No.: 247,983

[22] Filed: May 23, 1994

[51] Int. Cl.$^6$ .................................................. A61K 31/18
[52] U.S. Cl. .................... 514/604; 514/117; 514/305; 514/432; 514/444; 514/446; 514/448; 514/603; 514/605; 548/200; 548/201; 549/13; 549/23; 549/71; 549/72; 564/15; 564/86; 564/89; 564/91; 564/92
[58] Field of Search ...................... 514/117, 305, 514/432, 444, 446, 448, 603, 604, 605; 549/13, 23, 71, 72; 549/200, 201; 564/15, 86, 89, 91, 92

[56] References Cited

U.S. PATENT DOCUMENTS

| | | | |
|---|---|---|---|
| 5,063,208 | 11/1991 | Rosenberg et al. | 514/19 |
| 5,142,056 | 8/1992 | Kempe et al. | 546/265 |
| 5,157,041 | 10/1992 | Handa et al. | 514/314 |
| 5,196,438 | 3/1993 | Martin et al. | 514/311 |
| 5,204,471 | 4/1993 | Negele et al. | 546/144 |
| 5,235,039 | 8/1993 | Heath, Jr. et al. | 530/328 |
| 5,463,104 | 10/1995 | Vasquez et al. | 564/89 |

FOREIGN PATENT DOCUMENTS

| | | |
|---|---|---|
| 2075666 | 2/1993 | Canada. |
| 0337714 | 10/1989 | European Pat. Off.. |
| 0346847A2 | 12/1989 | European Pat. Off.. |
| 0356223A2 | 2/1990 | European Pat. Off.. |
| 0361341A2 | 4/1990 | European Pat. Off.. |
| 0402646 | 12/1990 | European Pat. Off.. |
| 0432695A2 | 6/1991 | European Pat. Off.. |
| 0432694A2 | 6/1991 | European Pat. Off.. |
| 043465A2 | 6/1991 | European Pat. Off.. |
| 0490667 | 6/1992 | European Pat. Off.. |
| 0498680A1 | 8/1992 | European Pat. Off.. |
| 0526009A1 | 2/1993 | European Pat. Off.. |
| 0533000A1 | 3/1993 | European Pat. Off.. |
| 0539192A1 | 4/1993 | European Pat. Off.. |
| 0560268A1 | 9/1993 | European Pat. Off.. |
| WO91/08221 | 6/1991 | WIPO. |
| WO93/04043 | 3/1993 | WIPO. |
| WO93/13066 | 7/1993 | WIPO. |
| WO93/23379 | 11/1993 | WIPO. |
| WO94/04492 | 3/1994 | WIPO. |
| WO94/05639 | 3/1994 | WIPO. |

OTHER PUBLICATIONS

Tam et al., J. Med. Chem., 35(7):1318–1320 (1992).
Huff, J. Med. Chem., 34(8):2305–2314 (1991).
Ghosh et al., J. Med. Chem., 36(2):292–294 (1993).
Ghosh et al., J. Med. Chem., 36(16):2300–2310 (1993).
Thompson et al., J. Am. Chem. Soc., 115(2):801–802 (1993).
Rich et al., J. Med. Chem., 34(3):1222–1225 (1991).
Thaisvivongs et al., J. Med. Chem., 34:2344–2356 (1991).
Ghosh et al., J. Med. Chem., 36:924–927 (1993).
Chong et al., J. Med. Chem., 36:2575–2577 (1993).
Vava Pradad et al., Peptides, Chemistry and Biology, Proceedings of the Twelfth American Peptide Symposium, Jun. 16–21, pp. 721–722 (1991).
Rich, et al., Chem. Abstracts, 114(15) Abstract No. 143998q (1991).
Houpis et al., Tetrahedron Letters, 34(16):2593–2596 (1993).
Roberts, N. A. et al., Science, 248:358–361 (1990).
Gilbert et al., J. Chem. Soc. Perkin Trans., 2:475–479 (1993).
Young et al., J. Med. Chem., 35:1702–1709 (1992).
Lyle et al., J. Med. Chem., 34:1228–1230 (1991).

*Primary Examiner*—Peter O'Sullivan
*Attorney, Agent, or Firm*—Finnegan, Henderson, Farabow, Garrett & Dunner

[57] ABSTRACT

HIV protease inhibitors, obtainable by chemical synthesis, inhibit or block the biological activity of the HIV protease enzyme, causing the replication of the HIV virus to terminate. These compounds, as well as pharmaceutical compositions that contain these compounds and optionally other anti-viral agents as active ingredients, are suitable for treating patients or hosts infected with the HIV virus, which is known to cause AIDS.

30 Claims, No Drawings

HIV PROTEASE INHIBITORS

BACKGROUND OF THE INVENTION

This invention relates to a novel series of chemical compounds useful as HIV protease inhibitors and to the use of such compounds as antiviral agents.

Acquired Immune Deficiency Syndrome (AIDS) is a relatively newly recognized disease or condition. AIDS causes a gradual breakdown of the body's immune system as well as progressive deterioration of the central and peripheral nervous systems. Since its initial recognition in the early 1980's, AIDS has spread rapidly and has now reached epidemic proportions within a relatively limited segment of the population. Intensive research has led to the discovery of the responsible agent, human T-lymphotropic retrovirus III (HTLV-III), now more commonly referred to as the human immunodeficiency virus or HIV.

HIV is a member of the class of viruses known as retroviruses. The retroviral genome is composed of RNA which is converted to DNA by reverse transcription. This retroviral DNA is then stably integrated into a host cell's chromosome and, employing the replicative processes of the host cells, produces new retroviral particles and advances the infection to other cells. HIV appears to have a particular affinity for the human T-4 lymphocyte cell which plays a vital role in the body's immune system. HIV infection of these white blood cells depletes this white cell population. Eventually, the immune system is rendered inoperative and ineffective against various opportunistic diseases such as, among others, pneumocystic carini pneumonia, Karposis sarcoma, and cancer of the lymph system.

Although the exact mechanism of the formation and working of the HIV virus is not understood, identification of the virus has led to some progress in controlling the disease. For example, the drug azidothymidine (AZT) has been found effective for inhibiting the reverse transcription of the retroviral genome of the HIV virus, thus giving a measure of control, though not a cure, for patients afflicted with AIDS. The search continues for drugs that can cure or at least provide an improved measure of control of the deadly HIV virus.

Retroviral replication routinely features post-translational processing of polyproteins. This processing is accomplished by virally encoded HIV protease enzyme. This yields mature polypeptides that will subsequently aid in the formation and function of infectious virus. If this molecular processing is stifled, then the normal production of HIV is terminated. Therefore, inhibitors of HIV protease may function as anti-HIV viral agents.

HIV protease is one of the translated products from the HIV structural protein pol gene. This retroviral protease specifically cleaves other structural polypeptides at discrete sites to release these newly activated structural proteins and enzymes, thereby rendering the virion replication-competent. As such, inhibition of the HIV protease by potent compounds may prevent proviral integration of infected T-lymphocytes during the early phase of the HIV-1 life cycle, as well as inhibit viral proteolytic processing during its late stage. Additionally, the protease inhibitors may have the advantages of being more readily available, longer lived in virus, and less toxic than currently available drugs, possibly due to their specificity for the retroviral protease.

In accordance with this invention, there is provided a novel class of chemical compounds that can inhibit and/or block the activity of the HIV protease, which halts the proliferation of HIV virus, pharmaceutical compositions containing these compounds, and the use of the compounds as inhibitors of the HIV protease.

SUMMARY OF THE INVENTION

The present invention relates to compounds falling within formula (1) below, and pharmaceutically acceptable salts thereof, that inhibit the protease encoded by human immunodeficiency virus (HIV) type 1 (HIV-1) or type 2 (HIV-2). These compounds are useful in the treatment of infection by HIV and the treatment of the acquired immune deficiency syndrome (AIDS). The compounds of formula 1, their pharmaceutically acceptable salts, and the pharmaceutical compositions of the present invention can be used alone or in combination with other antivirals, immunomodulators, antibiotics or vaccines. Compounds of the present invention can also be used as prodrugs. Methods of treating AIDS, methods of treating HIV infection and methods of inhibiting HIV protease are disclosed.

The compounds of the present invention are of the formula (1):

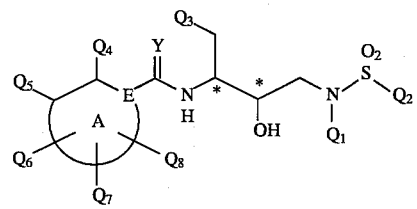

wherein:

$Q_1$ is selected from substituted or unsubstituted carbocycle, heterocycle, alkyl, alkynyl, and alkenyl;

$Q_2$ is selected from hydroxyl, halogen, hydrolyzable group, and substituted and unsubstituted carbocycle, heterocycle, alkyl, alkoxyl, carbocyclyloxyl, heterocyclyloxyl, amino, acyl, alkynyl, and alkenyl;

$Q_3$ is selected from mercapto, substituted aryl or aryloxyl, and substituted or unsubstituted thioether, amino, and partially saturated heterocyle;

$Q_4$–$Q_8$, when present, are independently selected from hydrogen, hydroxyl, mercapto, dioxide, nitro, halogen, —O—J, wherein J is a substituted or unsubstituted hydrolyzable group, and substituted and unsubstituted alkoxyl, aryloxyl, thioether, acyl, sulfinyl, sulfonyl, amino, alkyl, cycloalkyl, akenyl, alkynyl, saturated and partially saturated heterocycle and aryl, and further wherein any one or more of $Q_4$–$Q_8$ may be a member of a spiro ring and any two of $Q_4$–$Q_8$ may together be members of a ring;

Y is selected from oxygen, —N—H, —N-alkyl, —N-alkenyl, —N-alkynyl, sulfur, selenium, and two hydrogen atoms;

E is carbon or nitrogen; and

A is a carbocycle or heterocycle, which is optionally further substituted;

or a pharmaceutically acceptable salt thereof.

Preferred species of the formula (1) are: N-[(2 syn,3S)-2-Hydroxy-4-phenylthio-3-(2'methyl-3'-hydroxyphenyl) carboxamide-butyl]-N-isobutyl-4-methoxy-benzenesulfonamide, and its pharmaceutically acceptable salts, and its prodrug analogs; N-[(2 syn,3S)-2-Hydroxy-4-phenylthio-3-(2'methyl-3'-hydroxyphenyl) carboxamide-butyl]-N-isobutyl-4-hydroxy-benzenesulfonamide, and its pharmaceutically acceptable salts, and its prodrug analogs; N-Cyclopentylmethyl- 4-hydroxy-N-((2 syn,3S)-2-hydroxy-4-phenylthio- 3-(2'-methyl-3'-hydroxyphenyl) carboxamide-butyl)benzenesulfonamide, and its pharmaceutically acceptable salts, and its prodrug analogs; N-Cyclopentylmethyl-4-amino-N-((2 syn,3S)-2 -hydroxy-4-phenylthio-3-(2'-methyl-3'-hydroxyphenyl) carboxamide-butyl)-benzenesulfonamide, and its pharmaceutically acceptable salts, and its prodrug analogs; and N-[(2 syn,3S)-2-Hydroxy-4 -phenylthio-3-(2'methyl-3'-hydroxyphenyl) carboxamide-butyl]-N-cyclohexylmethyl- 4-methoxy-benzenesulfonamide, and its pharmaceutically acceptable salts, and its prodrug analogs.

The present invention further provides pharmaceutical formulations comprising an effective amount of a compound of formula (1) or a pharmaceutically acceptable salt thereof, in combination with a pharmaceutically acceptable carrier, such as a diluent or excipient.

The present invention further provides a method of treating AIDS comprising administering to a host or patient, such as a primate, an effective amount of a compound of the present invention.

The present invention further provides a method of inhibiting HIV replication comprising administering to an HIV infected cell, a cell susceptible to HIV infection or a host or patient, such as a primate, an effective amount of a compound of the present invention.

DETAILED DESCRIPTION OF THE INVENTION

The present invention provides new compounds falling within formula (1), as described above, that are useful for treating HIV infection and/or AIDS. Compounds can also be made in which $Q_3$ is replaced by $Q_{3a}$ and $Q_{3a}$ represents mercapto and substituted and unsubstituted alkoxyl, aryloxyl, thioether, amino, alkyl, cycloalkyl, saturated and partially saturated heterocycle, and aryl.

Compounds of the formula (1) may be prodrugs. For example, compounds wherein at least one of $Q_4$–$Q_8$ is —O—J and/or when Q2 has a substituent —O—J, as defined above, may be used as prodrugs, which can serve to improve the pharmaceutical properties of the compounds, such as pharmacokinetic properties, for example, improved bioavailability or solubility. The preparation of the prodrugs may be carried out by reacting a compound of the formula (1), wherein, for example, at least one of $Q_4$–$Q_8$ is —O—H and/or Q2 has a substituent —O—H, with, for example, an activated amino acyl, phosphoryl or hemisuccinyl derivative.

All temperatures stated herein are in degrees Celsius (°C.). All units of measurement employed herein are in weight units except for liquids which are in volume units.

The term "alkyl" as used herein refers to straight or branched chain groups, preferably, having one to eight, more preferably having one to six, and most preferably having from one to four carbon atoms. The term "$C_1$–$C_6$ alkyl" represents a straight or branched alkyl chain having from one to six carbon atoms. Exemplary $C_1$–$C_6$ alkyl groups include methyl, ethyl, n-propyl, isopropyl, butyl, isobutyl, sec-butyl, t-butyl, pentyl, neo-pentyl, hexyl, isohexyl, and the like. The term "$C_1$–$C_6$ alkyl" includes within its definition the term "$C_1$–$C_4$ alkyl".

The term "cycloalkyl" represents a saturated or partially saturated, mono- or poly-carbocyclic ring, preferably having 5–14 ring carbon atoms. Exemplary cycloalkyls include monocyclic rings having from 3–7, preferably 3–6, carbon atoms, such as cyclopropyl, cyclobutyl, cyclopentyl, cyclohexyl, cycloheptyl and the like. An exemplary cycloalkyl is a $C_5$–$C_7$ cycloalkyl, which is a saturated hydrocarbon ring structure containing from five to seven carbon atoms.

The term "alkoxyl" represents —O-alkyl. An example of an alkoxyl is a $C_1$–$C_6$ alkoxyl, which represents a straight or branched alkyl chain having from one to six carbon atoms attached to an oxygen atom. Exemplary $C_1$–$C_6$ alkoxyl groups include methoxyl, ethoxyl, propoxyl, isopropoxyl, butoxyl, sec-butoxyl, t-butoxyl, pentoxyl, hexoxyl, and the like. $C_1$–$C_6$ alkoxyl includes within its definition a $C_1$–$C_4$ alkoxyl.

The term "alkenyl" as used herein refers to a class of acyclic unsaturated hydrocarbons having one or more double bonds.

The term "alkynyl" as used herein refers to a class of acyclic unsaturated hydrocarbons having one or more triple bonds.

The term "aryl" as used herein refers to a carbocyclic or heterocyclic, aromatic, 5–14 membered monocyclic or polycyclic ring. Exemplary aryls include phenyl, naphthyl, anthryl, phenanthryl, thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, triazinyl, benzo[b]thienyl, naphtho[2,3-b]thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl.

The term "aryloxyl" represents —O-aryl.

The term "hydrolyzable group" is a group, which when bonded to an oxygen, forms an ester, which can be hydrolyzed in vivo to a hydroxyl group. Exemplary hydrolyzable groups, which are optionally substituted, include acyl function, sulfonate function and phosphate function. For example, such hydrolyzable groups include blocked or unblocked amino acid residue, a hemisuccinate residue, and a nicotinate residue.

The term "halogen" represents chlorine, fluorine, bromine or iodine. The term "halo" represents chloro, fluoro, bromo or iodo.

The term "carbocycle" represents an aromatic or a saturated or a partially saturated 5–14 membered monocyclic or polycyclic ring, such as a 5- to 7-membered monocyclic or 7- to 10-membered bicyclic ring, wherein all the ring members are carbon atoms. An example of a carbocycle is phenyl.

The term "heterocycle" represents an aromatic or a saturated or a partially saturated, 5–14 membered, monocylic or polycyclic ring, such as a 5- to 7-membered monocyclic or 7- to 10-membered bicyclic ring, having from one to three heteroatoms selected from nitrogen, oxygen and sulfur, and wherein any nitrogen and sulfur heteroatoms may optionally be oxidized, and any nitrogen heteroatom may optionally be quaternized. The heterocyclic ring may be attached at any suitable heteroatom or carbon atom. Examples of such heterocycles include decahydroisoquinolinyl, octahydrothieno[3,2-c]pyridinyl, piperidinyl, piperazinyl, azepinyl, pyrrolyl, pyrrolidinyl, pyrazolyl, pyrazolidinyl, imidazolyl, isobenzofuranyl, furazanyl, imidazolinyl, imidazolidinyl, pyridyl, pyrazinyl, pyrimidinyl, pyridazinyl, oxazolyl, oxazolidinyl, isoxazolyl, thianthrenyl, triazinyl, isoxazolidinyl, morpholinyl, thiazolyl, thiazolidinyl, isothiazolyl, quinuclidinyl, isothiazolidinyl, indolyl, quinolinyl, chromenyl, xanthenyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, benzo[b]thienyl, naphtho[2,3-b]thienyl, thiamorpholinyl, thiamorpholinylsulfoxide, thiamorpholinylsulfone, oxadiazolyl, triazolyl, tetrahydroquinolinyl, tetrahydrisoquinolinyl, phenoxathienyl, indolizinyl, isoindolyl, indazolyl, purinyl, isoquinolyl, quinolyl, phthalazinyl, naphthyridinyl, quinoxalinyl, quinzolinyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl.

The term "carbocyclyloxyl" represents carbocycle-O.

The term "heterocyclyloxyl" represents heterocycle-O.

The term "thioether" includes S-aryl, such as phenylthio and naphthylthio; S-heterocycle where the heterocycle is saturated or partially saturated; S-($C_5$-$C_7$)-cycloalkyl; and S-alkyl, such as $C_1$-$C_6$ alkylthio. In the thioether, the -aryl, the -heterocycle, the -cycloalkyl and the -alkyl can optionally be substituted. An example of a thioether is "$C_1$-$C_6$ alkylthio", which represents a straight or branched alkyl chain having from one to six carbon atoms attached to a sulfur atom. Exemplary $C_1$-$C_6$ alkylthio groups include methylthio, ethylthio, propylthio, isopropylthio, butylthio, sec-butylthio, t-butylthio, pentylthio, hexylthio, and the like.

The term "mercapto" represents —SH.

The term "amino" represents —$NL_1L_2$, wherein $L_1$ and $L_2$ are preferably independently selected from carbocycle, heterocycle, alkyl, sulfonyl, alkoxyl, carbocyclyloxyl, heterocyclyloxyl and hydrogen; or $NC(O)L_3$, wherein $L_3$ is preferably alkyl, alkoxyl, hydrogen or —$NL_1L_2$. The carbocycle, heterocycle, alkyl and alkoxyl groups can optionally be substituted. An example of an amino is $C_1$-$C_4$ alkylamino, which represents a straight or branched alkyl chain having from one to four carbon atoms attached to an amino group. Exemplary $C_1$-$C_4$ alkylamino groups include methylamino, ethylamino, propylamino, isopropylamino, butylamino, sec-butylamino, and the like. Another example of an amino is di($C_1$-$C_4$)alkylamino, which represents two straight or branched alkyl chains, each having from one to four carbon atoms attached to a common amino group. Exemplary di($C_1$-$C_4$)alkylamino groups include dimethylamino, ethylmethylamino, methylpropylamino, ethylisopropylamino, butylmethylamino, sec-butylethylamino, and the like. An example of an amino is $C_1$-$C_4$ alkylsulfonylamino, which has a straight or branched alkyl chain having from one to four carbon atoms attached to a sulfonylamino moiety. Exemplary $C_1$-$C_4$ alkylsulfonylamino groups include methylsulfonylamino, ethylsulfonylamino, propylsulfonylamino, isopropylsulfonylamino, butylsulfonylamino, sec-butylsulfonylamino, t-butylsulfonylamino, and the like.

The term "acyl" represents $L_6C(O)L_4$, wherein $L_6$ is a single bond, —O or —$NL_1$, wherein $L_1$ is as defined above, and further wherein $L_4$ is preferably alkyl, amino, hydroxyl, alkoxyl or hydrogen. The alkyl and alkoxyl groups can optionally be substituted. An exemplary acyl is a $C_1$-$C_4$ alkoxycarbonyl, which is a straight or branched alkoxyl chain having from one to four carbon atoms attached to a carbonyl moiety. Exemplary $C_1$-$C_4$ alkoxycarbonyl groups include methoxycarbonyl, ethoxycarbonyl, propoxycarbonyl, isopropoxycarbonyl, butoxycarbonyl, and the like. Another exemplary acyl is a carboxy wherein $L_6$ is a single bond and $L_4$ is alkoxyl, hydrogen, or hydroxyl. A further exemplary acyl is N-($C_1$-$C_4$)alkylcarbamoyl ($L_6$ is a single bond and $L_4$ is an amino), which is a straight or branched alkyl chain having from one to four carbon atoms attached to the nitrogen atom of a carbamoyl moiety. Exemplary N-($C_1$-$C_4$)alkylcarbamoyl groups include N-methylcarbamoyl, N-ethylcarbamoyl, N-propylcarbamoyl, N-isopropylcarbamoyl, N-butylcarbamoyl, and N-t-butylcarbamoyl, and the like. Yet another exemplary acyl is N,N-di($C_1$-$C_4$)alkylcarbamoyl, which has two straight or branched alkyl chains, each having from one to four carbon atoms attached to the nitrogen atom of a carbamoyl moiety. Exemplary N,N-di($C_1$-$C_4$)alkylcarbamoyl groups include N,N-dimethylcarbamoyl, N,N-ethylmethylcarbamoyl, N,N-methylpropylcarbamoyl, N,N-ethylisopropylcarbamoyl, N,N-butylmethylcarbamoyl, N,N-sec-butylethylcarbamoyl, and the like.

The term "sulfinyl" represents —SO—$L_5$, wherein $L_5$ is preferably alkyl, amino, aryl, cycloalkyl or heterocycle. The alkyl, aryl, cycloalkyl and heterocycle can all optionally be substituted.

The term "sulfonyl" represents —SO—$L_5$, wherein $L_5$ is preferably alkyl, aryl, cycloalkyl, heterocycle or amino. The alkyl, aryl, cycloalkyl and heterocycle can all optionally be substituted. An example of a sulfonyl is a $C_1$-$C_4$ alkylsulfonyl, which is a straight or branched alkyl chain having from one to four carbon atoms attached to a sulfonyl moiety. Exemplary $C_1$-$C_4$ alkylsulfonyl groups include methylsulfonyl, ethylsulfonyl, propylsulfonyl, isopropylsulfonyl, butylsulfonyl, sec-butylsulfonyl, t-butylsulfonyl and the like.

As indicated above, many of the groups are optionally substituted. Examples of substituents for alkyl, alkenyl, alkynyl, and aryl include mercapto, thioether, nitro ($NO_2$), amino, aryloxyl, halogen, hydroxyl, alkoxyl, and acyl, as well as aryl, cycloalkyl and saturated and partially saturated heterocycles. Examples of substituents for heterocycle and cycloalkyl include those listed above for alkyl and aryl, as well as aryl and alkyl.

Exemplary substituted aryls include a phenyl or naphthyl ring substituted with one or more substituents, preferably one to three substituents, independently selected from halo, hydroxy, morpholino($C_1$-$C_4$)alkoxy carbonyl, pyridyl ($C_1$-$C_4$)alkoxycarbonyl, halo ($C_1$-$C_4$)alkyl, $C_1$-$C_4$ alkyl, $C_1$-$C_4$ alkoxy, carboxy, $C_1$-$C_4$ alkoxycarbonyl, carbamoyl, N-($C_1$-$C_4$)alkylcarbamoyl, amino, $C_1$-$C_4$alkylamino, di($C_1$-$C_4$)alkylamino or a group of the formula —$(CH_2)_a$—$R^7$ where a is 1, 2, 3 or 4; and $R^7$ is hydroxy, $C_1$-$C_4$ alkoxy, carboxy, $C_1$-$C_4$ alkoxycarbonyl, amino, carbamoyl, $C_1$-$C_4$ alkylamino or di($C_1$-$C_4$)alkylamino.

Another substituted alkyl is halo($C_1$-$C_4$)alkyl, which represents a straight or branched alkyl chain having from one to four carbon atoms with 1–3 halogen atoms attached to it. Exemplary halo($C_1$-$C_4$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like.

Another substituted alkyl is hydroxy($C_1$-$C_4$)alkyl, which represents a straight or branched alkyl chain having from one to four carbon atoms with a hydroxy group attached to it. Exemplary hydroxy($C_1$-$C_4$)alkyl groups include hydroxymethyl, 2-hydroxyethyl, 3-hydroxypropyl, 2-hydroxyisopropyl, 4-hydroxybutyl and the like.

Yet another substituted alkyl is $C_1$-$C_4$ alkylthio($C_1$-$C_4$)alkyl, which is a straight or branched $C_1$-$C_4$ alkyl group with a $C_1$-$C_4$ alkylthio group attached to it. Exemplary $C_1$-$C_4$ alkylthio($C_1$-$C_4$)alkyl groups include methylthiomethyl, ethylthiomethyl, propylthiopropyl, sec-butylthiomethyl, and the like.

Yet another exemplary substituted alkyl is heterocycle($C_1$–$C_4$)alkyl, which is a straight or branched alkyl chain having from one to four carbon atoms with a heterocycle attached to it. Exemplary heterocycle($C_1$–$C_4$)alkyls include pyrrolylmethyl, quinolinylmethyl, 1-indolylethyl, 2-furylethyl, 3-thien-2-ylpropyl, 1-imidazolylisopropyl, 4-thiazolylbutyl and the like.

Yet another substituted alkyl is aryl($C_1$–$C_4$)alkyl, which is a straight or branched alkyl chain having from one to four carbon atoms with an aryl group attached to it. Exemplary aryl($C_1$–$C_4$)alkyl groups include phenylmethyl, 2-phenylethyl, 3-naphthyl-propyl, 1-naphthylisopropyl, 4-phenylbutyl and the like.

The heterocycle can, for example, be substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N-($C_1$–$C_4$)alkylcarbamoyl, amino, $C_1$–$C_4$alkylamino, di($C_1$–$C_4$)alkylamino or a group having the structure —$(CH_2)_a$—$R^7$ where a is 1, 2, 3 or 4 and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino.

Examples of substituted heterocycles include 3-N-t-butyl carboxamide decahydroisoquinolinyl, 6-N-t-butyl carboxamide octahydro-thieno[3,2-c]pyridinyl, 3-methylimidazolyl, 3-methoxypyridyl, 4-chloroquinolinyl, 4-aminothiazolyl, 8-methylquinolinyl, 6-chloroquinoxalinyl, 3-ethylpyridyl, 6-methoxybenzimidazolyl, 4-hydroxyfuryl, 4-methylisoquinolinyl, 6,8-dibromoquinolinyl, 4,8-dimethylnaphthyl, 2-methyl-1,2,3,4-tetrahydroisoquinolinyl, N-methyl-quinolin-2-yl, 2-t-butoxycarbonyl-1,2,3,4-isoquinolin-7-yl and the like.

Exemplary heterocyclic ring systems represented by A or B include (1) 5-membered monocyclic ring groups such as thienyl, pyrrolyl, imidazolyl, pyrazolyl, furyl, isothiazolyl, furazanyl, isoxazolyl, thiazolyl and the like; (2) 6-membered monocyclic groups such as pyridyl, pyrazinyl, pyrimidinyl, pyridazinly, triazinyl and the like; and (3) polycyclic heterocyclic rings groups, such as decahydroisoquinolinyl, octahydro-thieno [3,2-c]pyridinyl, benzo[b]thienyl, naphtho [2,3-b]thianthrenyl, isobenzofuranyl, chromenyl, xanthenyl, and fully or partially saturated analogs thereof.

A cycloalkyl may be optionally substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N-($C_1$–$C_4$)alkylcarbamoyl, amino, $C_1$–$C_4$ alkylamino, di($C_1$–$C_4$)alkylamino or a group having the structure —$(CH_2)_a$—$R^7$ where a is 1, 2, 3 or 4 and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino. Exemplary substituted cycloalkyl groups include 3-methylcyclopentyl, 4-ethoxycyclohexyl, 5-carboxycyclo-heptyl, 6-chlorocyclohexyl and the like.

Exemplary substituted hydrolyzable groups include N-benzyl glycyl, N-Cbz-L-valyl, and N-methyl nicotinate.

The compounds of the present invention have at least two asymmetric centers denoted by an asterisk in the formula (1) below:

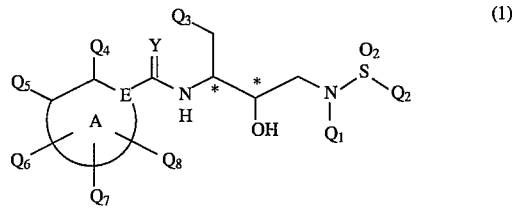

As a consequence of these asymmetric centers, the compounds of the present invention can occur in any of the possible stereoisomeric forms, and can be used in mixtures of stereoisomers, which can be optically active or racemic, or can be used alone as essentially pure stereisomers, i.e., at least 95% pure. All asymmetric forms, individual stereoisomers and combinations thereof, are within the scope of the present invention.

For the compounds of Formula 1, and intermediates thereof, the stereochemistry of the explicitly shown hydroxyl is defined relative to —$CH_2$—$Q_3$ on the adjacent carbon atom, when the molecule is drawn in an extended zig-zag representation (such as that drawn for compounds N-[(2 syn,3S)-2-Hydroxy-4-phenylthio-3-(2'methyl-3'-hydroxyphenyl) carboxamide-butyl]-N-isobutyl-4-methoxy-benzenesulfonamide; N-[(2 syn,3S)-2-Hydroxy-4-phenylthio-3-( 2'methyl-3'-hydroxyphenyl) carboxamide-butyl] -N-isobutyl-4 -hydroxy-benzenesulfonamide; N-Cyclopentylmethyl-4-hydroxy-N-((2 syn,3S)-2-hydroxy-4-phenylthio-3-(2'-methyl-3'-hydroxyphenyl) carboxamide-butyl)-benzenesulfonamide; N-Cyclopentylmethyl-4-amino-N-((2 syn,3S)-2-hydroxy-4-phenylthio-3-(2'-methyl-3'-hydroxyphenyl) carboxamide-butyl)-benzenesulfonamide; and N-[(2 syn,3S)-2-Hydroxy-4-phenylthio-3-(2'methyl-3'-hydroxyphenyl) carboxamide-butyl]-N-cyclohexylmethyl-4-methoxy-benzenesulfonamide. If both OH and —$CH_2$—$Q_3$ reside on the same side of the plane defined by the extended backbone of the compound, the stereochemistry of the hydroxyl will be referred to as "syn". If OH and —$CH_2$—$Q_3$ reside on opposite sides of that plane, the stereochemistry of the hydroxyl will be referred to as "anti".

Preferably, the compounds of the present invention are substantially pure, i.e, over 50% pure. More preferably, the compounds are at least 75% pure. Even more preferably, the compounds are more than 90% pure. Even more preferably, the compounds are at least 95% pure, more preferably, at least 97% pure, and most preferably at least 99% pure.

As mentioned above, the invention includes the pharmaceutically acceptable salts of the compounds defined by formula (1). A compound of this invention may possess a sufficiently acidic, a sufficiently basic, or both functional groups, and accordingly react with any of a number of inorganic or organic bases, and inorganic and organic acids, to form a pharmaceutically acceptable salt.

The term "pharmaceutically acceptable salt", as used herein, refers to salts of the compounds of the above formula which are substantially non-toxic to living organisms. Exemplary pharmaceutically acceptable salts include those salts prepared by reaction of the compounds of the present invention with a mineral or organic acid or an inorganic base. Such salts are known as acid addition and base addition salts.

Acids that may be employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like.

Examples of pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1, 4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, λ-hydroxybutyrate, glycollate, tartrate, methane-sulfonate, propanesulfonate, naphthalene-1-sulfonate, napthalene-2-sulfonate, mandelate and the like.

Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic and organic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds are:

N-[2-Hydroxy-4-phenylthio-3-(2' methyl-3'-hydroxyphenyl) carboxamide-butyl]-N-isobutyl-4-methoxy-benzenesulfonamide:

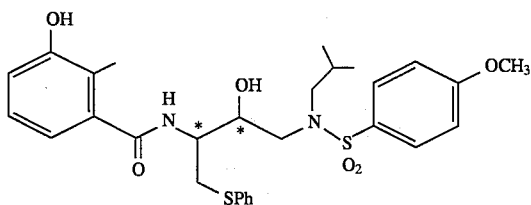

N-[2-Hydroxy-4-phenylthio-3-(2' methyl-3'-hydroxyphenyl) carboxamide-butyl]-N-isobutyl-4-hydroxy-benzenesulfonamide:

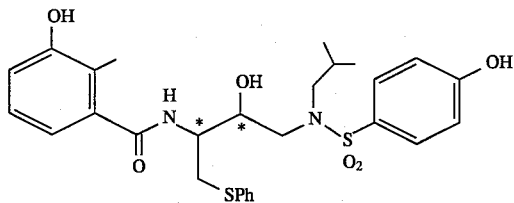

N-Cyclopentylmethyl-4-hydroxy-N-(2-hydroxy-4-phenylthio-3-(2'-methyl-3'-hydroxyphenyl) carboxamide-butyl)-benzenesulfonamide:

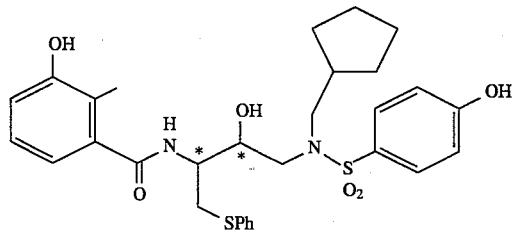

N-Cyclopentylmethyl-4-amino-N-(2-hydroxy-4-phenylthio-3-(2'-methyl-3'-hydroxyphenyl) carboxamide-butyl)-benzenesulfonamide:

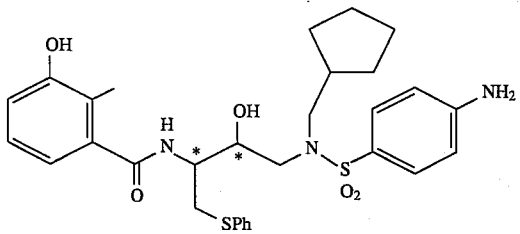

and

N-[2-Hydroxy-4-phenylthio-3-(2'methyl-3'-hydroxyphenyl) carboxamide-butyl]-N-cyclohexylmethyl-4-methoxy-benzenesulfonamide:

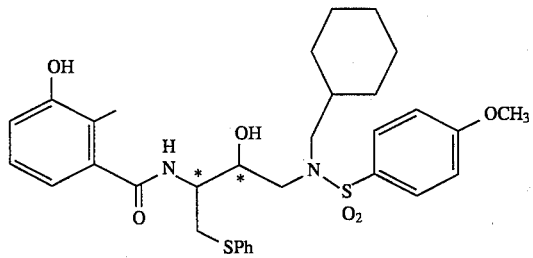

Each of the above five formulae has two assymetric centers and thus defines a compound selected from the group of four individual stereoisomers and any mixture of two or more stereoisomers.

Preferred stereisomers of these compounds are:

N-[(2 syn,3S) -2-Hydroxy-4-phenylthio-3-(2'methyl-3'-hydroxyphenyl) carboxamide-butyl]-N-isobutyl-4-methoxy-benzenesulfonamide:

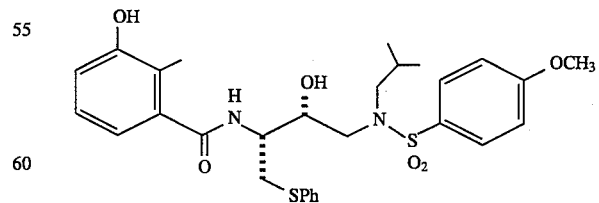

N-[(2 syn,3S)-2-Hydroxy-4-phenylthio-3-(2'methyl-3'-hydroxyphenyl) carboxamide-butyl]-N-isobutyl-4-hydroxybenzenesulfonamide:

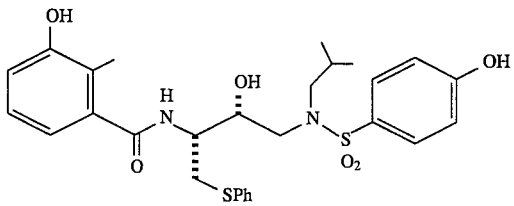

N-Cyclopentylmethyl-4-hydroxy-N-((2 syn,3S)-2-hydroxy-4-phenylthio-3-(2'-methyl-3'-hydroxyphenyl) carboxamide-butyl)benzenesulfonamide:

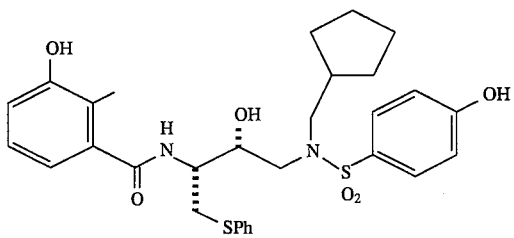

N-Cyclopentylmethyl-4-amino-N-((2 syn,3S)-2-hydroxy-4-phenylthio- 3-(2'-methyl-3'-hydroxyphenyl) carboxamide-butyl)-benzenesulfonamide:

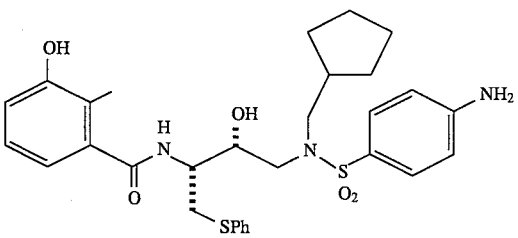

and
N-[(2 syn,3S)-2-Hydroxy-4-phenylthio-3-(2'methyl-3'-hydroxyphenyl) carboxamide-butyl]-N-cyclohexylmethyl-4-methoxy-benzenesulfonamide:

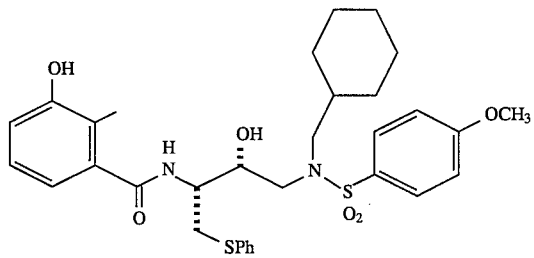

The following Preparations and Examples illustrate aspects of the invention. These examples are for illustrative purposes and are not intended to limit the scope of the invention.

Abbreviations for the terms melting point, nuclear magnetic resonance spectra, electron impact mass spectra, field desorption mass spectra, fast atom bombardment mass spectra, infrared spectra, ultraviolet spectra, elemental analysis, high performance liquid chromatography, and thin layer chromatography are, respectively, m.p., NMR, EIMS, MS(FD), MS(FAB), IR, UV, Analysis, HPLC, and TLC. In addition, the absorption maxima listed for the IR spectra are those of interest, not all maxima observed.

In conjunction with the NMR spectra, the following abbreviations are used: singlet (s), doublet (d), doublet of doublets (dd), triplet (t), quartet (q), multiplet (m), doublet of multiplets (dm), broad singlet (br.s), broad doublet (br.s), broad triplet (br.t), and broad multiplet (br.m). J indicates the coupling constant in Hertz (Hz). Unless otherwise noted, NMR data refer to the free base of the subject compound.

The NMR spectra were obtained on a Bruker Corp. 270 MHz instrument or on a General Electric QE-300 300 MHz instrument. The chemical shifts are expressed in delta values (ppm downfield from tetramethylsilane). MS(FD) spectra were taken on a Varian-MAT 731 Spectrometer using carbon dendrite emitters. Any EIMS spectra were obtained on a CEC 21-110 instrument from Consolidated Electrodynamics Corporation. Any MS(FAB) spectra were obtained on a VG ZAB-3 Spectrometer. Any IR spectra were obtained on a Perkin-Elmer 281 instrument. Any UV spectra were obtained on a Cary 118 instrument. TLC was carried out on E. Merck silica gel plates. Melting points are uncorrected.

The epoxide used in the following reactions may be synthesized using Reaction Scheme A.

Reaction Scheme A

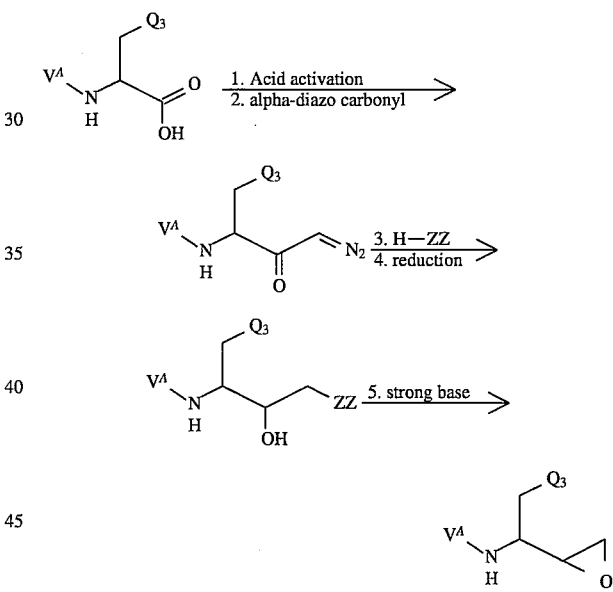

where:

$V^A$ is an amino-protecting group;

$Q^3$ is as defined above for formula (1); and

ZZ is halo.

Reaction Scheme A, above, is accomplished by carrying out reactions 1–5 in sequential order. Once a reaction is complete, the intermediate compound may be isolated, if desired, by procedures known in the art, for example, the compound may be crystallized and then collected by filtration, or the reaction solvent may be removed by extraction, evaporation or decantation. The intermediate compound may be further purified, if desired, by common techniques such a crystallization or chromatography over solid supports such as silica gel or alumina, before carrying out the next step of the reaction scheme.

Reaction A.1 is carried out by converting an amino-protected carboxylic acid reactant having the structure:

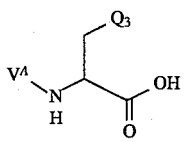

to the corresponding mixed anhydride under conditions known in the art. For example, the amino-protected carboxylic acid reactant may be reacted with a $C_1$–$C_6$ alkyl-chloroformate, such as isobutylchloroformate preferably in the presence of an acid scavenger. Preferred acid scavengers are the trialkylamines, preferably triethylamine. The reaction is typically carried out in an aprotic solvent such as ethyl acetate. Solvent choice is not critical so long as the solvent employed is inert to the ongoing reaction and the reactants are sufficiently solubilized to effect the desired reaction. The resulting mixed anhydride reactant is preferably used in Reaction A.2 without further isolation or purification.

Reaction A.2 is accomplished in two steps. First, a solution of sodium hydroxide, covered with a layer of an ether solvent, preferably diethyl ether, is reacted with a large excess of N-methyl-N-nitro-N-nitrosoguanidine to form a diazomethane reactant. The sodium hydroxide is preferably used as an aqueous solution having about four to six mol/liter of sodium hydroxide. Once this reaction is substantially complete, the organic layer is dried over a dessicant such as potassium hydroxide. This solution is then reacted with the mixed anhydride from Reaction A.1, above, to form the corresponding alpha-diazo carbonyl compound. The diazomethane reactant is preferably used in this reaction without isolation or purification. The reaction is typically carried out at a temperature of from about −50° C. to about −10° C., preferably about −20° C.

In Reaction A.3, the alpha-diazo carbonyl compound prepared in Reaction A.2 is reacted with an acid of the formula H—ZZ where ZZ is halo, in an aprotic solvent such as diethylether to form an alpha-halo carbonyl compound. A preferred acid reactant is hydrochloric acid which provides the corresponding alpha-chloro carbonyl compound. The reaction is typically carried out at a temperature from about −30° C. to about 0° C. Solvent choice is not critical so long as the solvent employed is inert to the ongoing reaction and the reactants are sufficiently solubilized to effect the desired reaction. The acid reactant is typically added in the form of an anhydrous gas in small increments until the reaction appears substantially complete. The reaction can be monitored by thin layer chromatography.

In Reaction A.4, the carbonyl moiety on the compound prepared in Reaction A.3 is reduced using standard conditions known in the art to form the corresponding alpha-chloro hydroxy compound. For example, the compound prepared in Reaction A.3 is combined with a reducing agent in a mixture of solvents. Typical reducing agents include sodium borohydride, lithium borohydride, zinc borohydride, diisobutylaluminum hydride, and sodium bis(2-methoxyethoxy) aluminum hydride. A preferred reducing agent is sodium borohydride. Typical solvent mixtures include a protic and aprotic mixture such as tetrahydrofuran/water. Solvent choice is not critical so long as the solvent employed is inert to the ongoing reaction and the reactants are sufficiently solubilized to effect the desired reaction. The reaction is typically carried out at a temperature from about −10° C., preferably about 0° C.

In Reaction A.5, the alpha-chloro hydroxy compound prepared in Reaction A.4 is treated with a strong base to form the corresponding epoxide (which is used above in Reaction I.5) under standard conditions known in the art. For example, the alpha-chloro hydroxy compound may be reacted with a potassium hydroxide/ethanol mixture in an alcoholic solvent such as ethanol. The reaction is typically carried out at a temperature from about 0° C. to about the reflux temperature of the solvent. Preferably the reaction is carried out at room temperature.

The epoxide from Scheme A can then be used to make compounds of Formula 1 using reaction Scheme B as follows (in Scheme B, the protecting group $V^A$ of the epoxide from Scheme A is specifically shown as

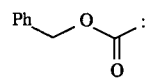

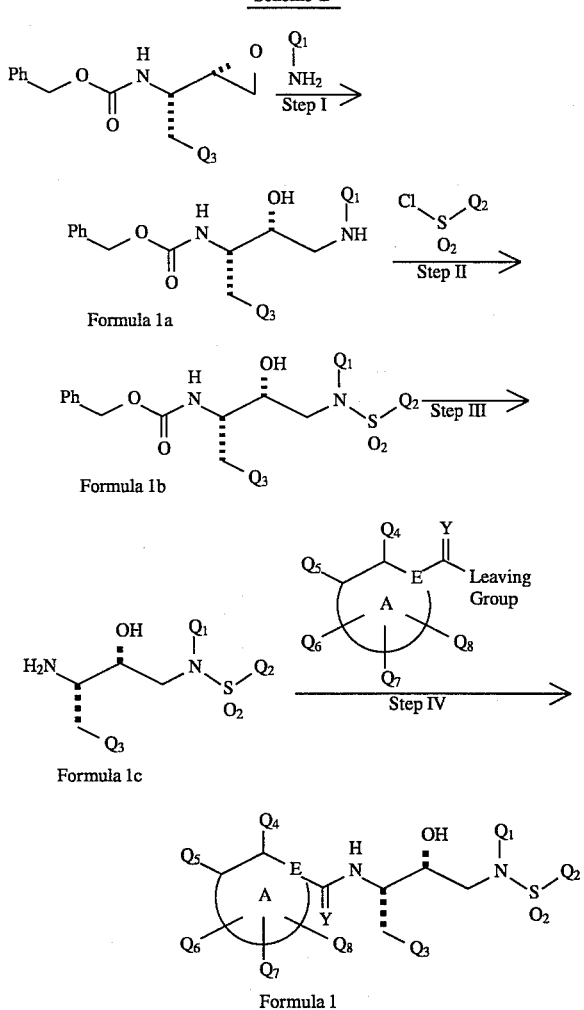

Step I in Scheme B can be performed as shown in the following examples or generally by reacting the epoxide prepared in Reaction A.5 with a heterocyclic reactant, H—X, in an alcoholic solvent at a temperature of from about 20° C. to 100° C. Solvent choice is not critical so long as the solvent employed is inert to the ongoing reaction and the reactants are sufficiently solubilized to effect the desired reaction. Typical solvents for this reaction include the alcohols, preferably isopropanol or ethanol. The reaction is preferably carried out at a temperature of about 80° C.

In Step II in Scheme B, compounds of Formula 1a may be converted to compounds of Formula 1b by reaction with sulfonyl-activated species to form sulfonamides, sulfonyl ureas, thiocarbamates and the like. Methods for preparing such sulfonyl-activated species are well within the ordinary skill of the art. Typically, sulfonyl halides are used to obtain sulfonamides. Many sulfonyl halides are commercially available; others may be easily obtained using conventional synthetic techniques (Gilbert, E. E. "Recent Developments in Preparative Sulfonation and Sulfation" Synthesis 1969: 3 (1969) and references cited therein; Hoffman, R. V. "M-Trifluoromethylbenzenesulfonyl Chloride" Org. Synth. Coll. Vol. VII, John Wiley and Sons (1990); Hartman, G. D. et. al. "4-Substituted Thiophene-and Furan-2-sulfonamides as Topical Carbonic Anhydrase Inhibitors" *J. Med. Chem.*, 35, p. 3822 (1992) and references cited therein. Sulfonyl ureas are usually obtained by the reaction of an amine with sulfuryl chloride or a suitable equivalent such as sulfuryl-bis-imidazole or sulfuryl-bis-N-methyl imidazole. Thiocarbamates are typically obtained by the reaction of an alcohol with sulfuryl chloride or a suitable equivalent such as sulfuryl-bis-imidazole or sulfuryl-bis-N-methyl imidazole.

Step III of Scheme B may be accomplished by removal of protecting groups from the amine by methods known to those skilled in the art. For example, protecting groups may be removed by methods described in Bodanszky and Bodanszky, "The practice of Peptide Synthesis", Springer-Verlag, Berlin, Germany (1984) and in the "The Peptides", Gross and Meinhofer (Eds); Academic Press, 1979, Vols. I–III, which are incorporated herein by reference, such as by hydrogenation in the presence of a palladium, platinum or rhodium catalyst, by treatment with sodium in liquid ammonia; hydrochloric, hydrofluoric, hydrobromic, formic, trifluoromethanesulfonic, or trifluoroacetic acid; secondary amines; fluoride ion; trimethylsilyl halides including bromide and iodide; or alkali. If desired, the methyl group of the methoxy phenyl sulfonamide can be removed by treatment with a Lewis acid or protic acid, e.g., $BBr_3$.

In Step IV of Scheme B, reaction of a compound of Formula 1c with an appropriate activated reagent will advantageously yield a compound of Formula 1. For instance, reaction with an activated carboxylate, such as an acyl halide (e.g., acid fluorides, acid chlorides, and acid bromides), an activated ester such nitrophenyl ester or 1-hydroxybenzotriazole (HOBT) ester, an anhydride such as the symmetrical anhydride or isobutyl anhydride, or mixed carbonic-phosphoric or carbonic-phosphinic anhydrides, will yield the corresponding amide.

It will be readily recognized that in order to facilitate specific reactions, the protection of one or more potentially reactive groups followed by subsequent removal of that group may be required. Such modification to the reaction schemes outlined above is within the ordinary skill of the art.

PREPARATION 1

2-Methyl-3-hydroxybenzoic acid

To a cold (0° C.) suspension of 0.54 g (3.3 mmol) of 2-methyl- 3-aminobenzoic acid in 5 mL of water containing 0.65 mL of concentrated sulfuric acid, was added 0.25 g (3.6 mmol) of solid sodium nitrite. After approximately 15 minutes the reaction mixture was poured into 20 mL of warm water containing 4 mL of concentrated sulfuric acid. The resultant reaction mixture was heated slowly to 90° C. resulting in gas evolution After the gas evolution ceased, the solution was cooled to room temperature and extracted with ethyl acetate. The organic layers were combined, washed with 0.5N hydrochloric acid, dried and concentrated under reduced pressure. The crude residue was purified by rapid filtration through silica gel (eluent of 5% methanol in methylene chloride) to yield 350 mg of a white solid (m.p. 137°–138° C.). Yield: 69%.

$^1$H NMR ($CDCl_3$): δ8.18 (br.s, 1H), 7.42 (d, J=7.7 Hz, 1H), 7.13 (t, J=7.9 Hz, 1H), 6.93 (d, J=7.9 Hz, 1H), 2.46 (s, 3H).

Analysis for $C_8H_8O_3$: Calcd: C, 63.15; H, 5.29; Found: C, 63.32; H, 5.36.

Alternatively, the desired subtitled compound was prepared by adding 22.6 g (0.33 mol) of sodium nitrite in small portions to a cooled (–10° C.) solution of 45 g (0.30 mol) of 3-amino-2-methylbenzoic acid and 106 g (58 mL; 1.08 mol) of concentrated sulfuric acid in 400 mL of water, while maintaining the temperature below 7° C. The resultant reaction mixture was stirred for approximately 30 minutes at –10° C., poured into a solution of 240 mL of concentrated sulfuric acid in 1.2 L water, and then slowly heated to 80° C. (heavy gas evolution occurs between the temperatures of 40°–60° C.). When the gas evolution stopped, the reaction mixture was cooled to room temperature and the subtitled compound was extracted five times with ethyl acetate (600 mL). The combined organic phases were combined with 500 mL of an aqueous saturated sodium carbonate solution. The resultant layers were separated and the aqueous layer was acidified to pH 2 with concentrated hydrochloric acid. The titled compound was then extracted using ethyl acetate (500 mL) and the combined organic phases were washed with brine, dried over sodium sulfate, filtered and then concentrated under reduced pressure to provide a crude material. This material was purified using two recrystallizations from an ethyl acetate/chloroform mixture to provide 23.2 g of a light orange powder. Yield: 52%.

PREPARATION 2

A. 2R-N(Benzyloxycarbonyl)amino-3-naphth-2-ylthio propanoic acid

To a solution of 1.28 g (8.00 mmol) of naphthalene-2-thiol in 30 mL of tetrahydrofuran, was slowly added 1.77 g (8.16 g) of 60% sodium hydride, under nitrogen. After stirring for approximately 15 minutes, a solution of N(benzyloxycarbonyl) serine-β-lactone in 20 mL of tetrahydrofuran was slowly added. The reaction mixture was allowed to react at room temperature for approximately one hour, and then was concentrated under reduced pressure to provide a residue. This residue was dissolved in ethyl acetate and washed sequentially with 0.5N sodium bisulfate and a saturated brine solution. The resulting layers were separated and the organic layer was dried over sodium sulfate, filtered, and then concentrated under reduced pressure to provide a residue. This residue was purified using flash chromatography to provide 2.08 g of a pale yellow solid. Yield: 68%.

$^1$H NMR ($CDCl_3$): δ3.42–3.61 (br.m, 2H), 5.53–5.76 (br.s, 1H), 4.85–5.08 (br.m, 2H), 5.54–5.76 (br.s, 1H), 7.06–7.97 (m, 12H).

$[\alpha]_D$ –55.72° (c 1.0, MeOH).

IR (KBr): 3348, 3048, 1746, 1715, 1674, 1560, 1550, 1269, 1200, 1060 $cm^{-1}$.

MS(FD): m/e 381 ($M^+$), 381 (100).

Analysis for $C_{20}H_{19}NO_4S$: Calcd: C, 66.12; H, 5.02; N, 3.67; Found: C, 66.22; H, 5.04; N, 3.86.

B. 3R-1-Diazo-2-oxo-3-N-(benzyloxycarbonyl)amino-4-(naphth-2-ylthio) butane

To a cold (−30° C.) solution of 15.38 g (40.3 mmol) of the subtitled compound of Preparation 2A in 230 mL of ethyl acetate, was slowly added 5.62 mL (40.3 mmol) of triethylamine, under nitrogen via syringe. To the resulting solution was then added 7.84 mL (60.5 mmol) of isobutyl chloroformate, via syringe. In a separate flask, 10 g of N(methyl)-N(nitro)-N(nitroso)-guanidine was carefully added to a bilayer mixture of 170 mL of diethylether and 170 mL of a 5N sodium hydroxide solution, resulting in a large evolution of gas. When this reaction was substantially complete, the organic layer was decanted from the aqueous layer onto potassium hydroxide and dried. This diazomethane formation and addition was repeated using identical quantities of diethylether and sodium hydroxide and 30 g of N(methyl)-N(nitro)-N(nitroso)guanidine. The resultant diazomethane reactant was then added to the mixed anhydride solution prepared above and the reaction mixture was allowed to react cold (−30° C.) for approximately 20 minutes. When the reaction was substantially complete, as indicated by TLC, nitrogen was bubbled through the solution using a fire polished Pasteur pipet to remove any excess diazomethane and then the solution was concentrated under reduced pressure to provide a residue. This residue was purified using flash chromatography (eluent of 10% ethyl acetate in methylene chloride) to provide 13.62 g of a yellow oil. Yield: 83%.

$^1$H NMR (CDCl$_3$): δ3.32–3.46 (m, 2H), 4.40–4.67 (m, 1H), 5.00–5.09 (m, 2H), 5.44 (s, 1H), 5.76 (d, J=7.8 Hz, 1H), 7.25–7.86 (m, 12H).

C. 3R-1-Chloro-2-oxo-3-N-(benzyloxycarbonyl)amino-4-(naphth-2-ylthio) butane

A short burst (about 2 seconds) of anhydrous hydrochloric acid (gas) was passed through a cold (−20° C.) solution of 13.62 g (33.59 mmol) of the subtitled compound of Preparation 2B in 230 mL of diethylether, resulting in the evolution of a gas. This procedure was repeated taking care not to add excess hydrochloric acid. When the reaction was substantially complete, as indicated by TLC, the solution was concentrated under reduced pressure to provide a residue. This residue was purified using flash chromatography (eluent of 10% ethyl acetate in methylene chloride) to provide 12.05 g of a pale tan solid. Yield: 87%.

$^1$H NMR (CDCl$_3$): δ3.41 (dd, J=12,6 Hz, 1H), 3.53 (dd, J=12,6 Hz, 1H), 4.18 (AB q, J=41.9 Hz, J=15.9 Hz, 2H), 4.77 (dd, J=9, 3 Hz, 1H), 5.04 (AB q, J=12 Hz, J=10.4 Hz, 2H), 5.59 (d, J=7 Hz, 1H), 7.24–7.85 (m, 12H).

[α]$_D$ −80.00° (c 1.0, MeOH).

IR (CHCl$_3$): 3426, 3031, 3012, 1717, 1502, 1340, 1230, 1228, 1045 cm$^{-1}$.

MS(FD): m/e 413 (M$^+$), 413 (100).

Analysis for C$_{22}$H$_{20}$NO$_3$SCl: Calcd: C, 63.84; H, 4.87; N, 3.38; Found: C, 64.12; H, 4.95; N, 3.54.

D. [3R-(3R*,4S*)]-1-Chloro-2-hydroxy-3-N-(benzyloxycarbonyl)amino- 4-(naphth-2-ylthio) butane To a cold (0° C.) solution of 530 mg (1.28 mmol) of the subtitled compound of Preparation 2C, in 10 mL of tetrahydrofuran and 1 mL of water, was added 73 mg (1.92 mmol) of sodium borohydride. When the reaction was substantially complete as indicated by TLC, the solution was adjusted to pH 3 using 10 mL of an aqueous saturated ammonium chloride solution and 500 μL of a 5N hydrochloric acid solution. The resultant solution was extracted twice with methylene chloride and the combined organic layers were washed with water, dried over sodium sulfate, filtered and then concentrated under reduced pressure to provide a residue. This residue was purified using radial chromatography (eluent of methylene chloride) to provide 212 mg of a tan solid. Yield: 40%.

$^1$H NMR (CDCl$_3$): δ3.40 (s, 2H), 3.61–3.71 (m, 2H), 3.97–3.99 (m, 2H), 4.99 (s, 2H), 5.16 (br.s, 1H), 7.21–7.83 (complex, 12H).

MS(FD): m/e 415 (M$^+$), 415 (100).

[α]$_D$ −47.67° (c 0.86, MeOH).

IR (CHCl$_3$): 3630, 3412, 3011, 1720, 1502, 1236, 1044 cm$^{-1}$.

Analysis for C$_{22}$H$_{22}$NO$_3$ClS: Calcd: C, 63.53; H, 5.33; N, 3.37; Found: C, 63.72; H, 5.60; N, 3.64.

E. [1'R-(1'R*,1S*)]-1-[(1'-N-(Benzyloxycarbonyl) amino-2'-(naphth-2-ylthio)ethyl]oxirane A solution of 31 mg (0.55 mmol) of potassium hydroxide in 1 mL of ethanol was added to a solution of 190 mg (0.46 mmol) of the subtitled compound of Preparation 2D, in 6 mL of a 1:2 ethanol/ethyl acetate solution. When the reaction was substantially complete, as indicated by TLC, the reaction mixture was poured into a water/methylene chloride mixture. The resulting layers were separated, and the organic layer was washed with water, dried over sodium sulfate, filtered and then concentrated under reduced pressure to provide a residue. This residue was purified using radial chromatography (eluent of 10% ethyl acetate in methylene chloride) to provide 172 mg of a light tan solid. Yield: 99%.

$^1$H NMR (CDCl$_3$): δ2.76 (br.s, 2H) 3.01 (br.s, 1H), 3.31 (d, J=5 Hz, 2H), 3.77 (br.s, 1H), 5.05 (s, 2H), 5.22 (d, J=6 Hz, 1H), 7.25–7.85 (complex, 12H).

[α]$_D$ −125.42° (c 0.59, MeOH).

MS(FD): m/e 379 (M$^+$), 379 (100).

IR (CHCl$_3$): 3640, 3022, 2976, 1720, 1502, 1235, 1045 cm$^{-1}$.

Analysis for C$_{22}$H$_{21}$NO$_3$S: Calcd: C, 69.63; H, 5.58; N, 3.69; Found: C, 69.41; H, 5.53; N, 3.64.

PREPARATION 3

A. 2R-2-N(Benzyloxycarbonyl)amino-3-phenylthio propanoic acid

The desired subtitled intermediate was prepared substantially in accordance with the procedure detailed in Procedure 2A, using 13.1 mL (127 mmol) of thiophenol, 4.6 g (117 mmol) of a 60% sodium hydride solution and 25.6 g (116 mmol) of L-N(benzyloxycarbonyl)-serine β-lactone in 450 mL of tetrahydrofuran to provide a residue. This residue was purified using flash chromatography (gradient eluent of 0–2% acetic acid in a 4:1 methylene chloride/ethyl acetate mixture) to provide 27.9 g of a white solid. Yield: 72%.

$^1$H NMR (CDCl$_3$): δ7.55–7.18 (m, 10H), 5.55 (d, J=7 Hz, 1H), 5.08 (s, 2H), 4.73–4.60 (m, 1H), 3.55–3.30 (m, 2H).

IR (KBr): 3304, 3035, 1687, 1532, 736 cm$^{-1}$.

MS(FD): m/e 332, 288, 271, 181.

Analysis for $C_{17}H_{17}NO_4S$: Calcd: C, 61.61; H, 5.17; N, 4.23; Found: C, 61.69; H, 5.22; N, 4.47.

Preparation 3A can be changed to the following procedure:

To a 2 L flask was added $Ph_3P$ (109.6 g) in 500 ml of $CH_2Cl_2$, and the mixture was cooled to −70° C. To the mixture was added a solution of diethylazidodicarboxylate (66 ml) in 60 ml of THF dropwise over 25 minutes. After 25 minutes, a solution of N-carbobenzyloxy-L-serine (100 g) in 400 ml of THF was added dropwise over 45 minutes and allowed to warm to room temperature in a water bath over two hours. 150 ml of THF was added to the mixture. In another flask, a solution of thiophenol (46 g) in 1 L of THF was cooled in an ice bath to 0° C. and treated portionwise with an NaH dispersion (10 g) to give a thick solution. After one hour, the crude lactone solution was added to the thiolate solution dropwise via an addition funnel over 30 minutes. After 12 hours, a white precipitate was filtered off, and the filter cake washed with THF. The solid was taken up in 0.4N $NaHSO_4$ and EtOAc, separated, and the organic layer was washed with brine, dried, and evaporated to afford 85 g of 2R-2-N-(benzyloxycarbonyl)amino- 3-phenylthio propanoic acid as a viscous oil.

The original solid is believed to be the sodium salt of the desired product. Thus, the yield and ease of isolation may be improved by isolation of the sodium salt directly.

B. 3S-1-Diazo-2-oxo-3-N-(benzyloxycarbonyl) amino-4-phenylthio butane

The desired subtitled compound was prepared substantially in accordance with the procedure detailed in Procedure 2B, using 12.1 g (37 mmol) of the subtitled compound of Preparation 3A, 5.09 mL (37 mmol) of triethylamine, 7.13 mL (55 mmol) isobutyl chloroformate, 146 mmol of a diazomethane solution to provide a residue. The diazomethane solution was prepared using 100 mL of diethylether, 150 mL of a 5N sodium hydroxide solution and 21 g (146 mmol) of N(methyl)-N(nitro)-N(nitroso)-guanidine as described in Preparation 2B. This residue was purified using flash chromatography (gradient eluent of 0–5% ethyl acetate in methylene chloride) to provide a yellow oil. Yield: 73%.

$^1$H NMR ($CDCl_3$): δ7.50–7.19 (m, 10H), 5.62 (d, J=7 Hz, 1H), 5.47 (br.s, 1H), 5.11 (s, 2H), 4.50–4.32 (m, 1H), 3.33 (d, J=6 Hz, 1H).

IR (KBr): 3012, 2115, 1720, 1501, 1367, 1228 $cm^{-1}$.

MS (FD): m/e 356, 328, 242.

C. 3R-1-Chloro-2-oxo-3-N-(benzyloxycarbonyl) amino-4-phenylthio butane

The desired subtitled compound was prepared substantially in accordance with the procedure detailed in Procedure 2C, using 22.3 g (63 mmol) of the subtitled compound of Preparation 3B and small quantities of hydrochloric acid (gas) in 400 mL of diethylether to provide 21 g of a white solid. This solid was used without further purification.

$^1$H NMR ($CDCl_3$): ^w 7.50–7.15 (m, 10H), 5.56 (dd, J=2,6.7 Hz, 1H), 5.11 (s, 2H), 4.78–4.67 (m, 1H), 4.20 (d, J=15.9 Hz, 1H), 4.12 (d, J=15.9 Hz, 1H), 3.48–3.23 (m, 2H).

IR (KBr): 3349, 1732, 1684, 1515, 1266 $cm^{-1}$.

MS (FD): m/e 363 ($M^+$).

Analysis for $C_{18}H_{18}NO_3SCl$: Calcd: C, 59.42; H, 4.99; N, 3.85; Found: C, 59.57; H, 5.09; N, 4.13.

D. [2S-(2R*,3S*)]-1-Chloro-2-hydroxy-3-N-(benzyoxycarbonyl)amino- 4-phenylthio butane The desired subtitled compound was prepared substantially in accordance with the procedure detailed in Procedure 2D, using 21 g (58 mmol) of the subtitled compound of Preparation 3C, 2.4 g (63 mmol) of sodium borohydride in 300 mL of tetrahydrofuran to provide a residue. This residue was purified using flash chromatography (gradient eluent of 0–2% methanol in methylene chloride) followed by flash chromatography (gradient eluent of 0–2% ethyl acetate in chloroform) and then recrystallized from methylene chloride at −78° C. to provide 8.3 g of the subtitled compound. Yield: 39%.

$^1$H NMR ($CDCl_3$): d 7.47–7.19 (m, 10H), 5.22–5.03 (m, 1H), 5.09 (s, 2H), 4.01–3.89 (m, 2H), 3.75–3.58 (m, 2H), 3.32 (d, J=4 Hz, 2H).

IR (KBr): 3321, 2951, 1688, 1542, 1246, 738 $cm^{-1}$.

MS (FD): m/e 366 ($M^+$), 119.

Analysis for $C_{18}H_{20}NO_3SCl$: Calcd: C, 59.09; H, 5.51; N, 3.83; Found: C, 59.03; H, 5.50; N, 3.96.

Preparation 3D can be changed to the following procedure:

The crude chloroketone 3R-1-Chloro-2-oxo-3-N-(benzyloxycarbonyl)amino- 4-phenylthio butane (16.87 g, 46.4 mmol) was added to 1 L absolute EtOH and 200 mL THF, and the solution was cooled in a $CO_2$-acetone bath (−78° $T_{int}$), and $NaBH_4$ (2.63 g, 69.5 mmol) in 200 ml absolute EtOH was added dropwise over 1 h ($T_{int}$<−75° C.). TLC analysis after the addition showed that the reaction was complete. The reaction was diluted with 300 mL ether and was quenched by the slow addition of 0.4N $NaHSO_3$ with stirring, which produced the evolution of gas. This mixture was concentrated under reduced pressure to remove most of the EtOH and additional water was added. The mixture was extracted with ether, and the combined organic layers were washed with saturated aqueous $NaHCO_3$ and brine, dried ($Na_2SO_4$), and concentrated to afford 15.7 g of an off white solid. This material was triturated with boiling hexane (300 mL), and the hexane was carefully decanted while hot. This was repeated 10 times (300 mL each) to provide 10.35 g of an off white solid (one pure isomer by TLC). The hexane filtrate was concentrated to give 6 g of white solid which was set aside. The triturated solid was heated with 50 mL $CH_2Cl_2$ and about 6 mL hexane and filtered hot. The clear solution was allowed to cool to 25° C. and was then placed in the freezer. The resulting solid was filtered and washed with hexanes to give 7.157 g of a white solid. The filtrate was combined with the hexane filtrate from above and with crude reaction product from two small scale experiments (500 mg starting ketone each), and the combined material was chromatographed on $SiO_2$ (2:1 hexanes-ether→1:1 hexanes-ether, loaded with $CH_2Cl_2$) to afford 2.62 g of additional product. A total of 10.31 g pure isomer of [2S-(2R*, 3S*)]-1-Chloro-2-hydroxy-3-N-(benzyloxycarbonyl)amino-4-phenylthio butane (50% yield from acid) was obtained.

alpha$_D$=−63.6° (c=1, MeOH).

E. [1'R-(1'R*,1S*)]-1-[(1'-N-(benzyoxycarbonyl)amino-2'-phenylthio)ethyl oxirane The desired subtitled compound was prepared substantially in accordance with the procedure detailed in Procedure 2E, using 8.3 g (23 mmol) of the subtitled compound of Preparation 3D, 1.4 g (25 mmol) of potassium hydroxide in 400 mL of ethanol to provide a residue. This residue was purified using flash chromatography (gradient eluent of 0–2% ethyl acetate in methylene chloride) to provide 6.4 g of a white solid. Yield: 85%.

$^1$H NMR (CDCl$_3$): δ7.45–7.15 (m, 10 H), 5.12 (s, 1H), 5.08 (s, 2H), 3.77–3.62 (m, 1H), 3.21 (d, J=6 Hz, 2H), 2.99 (m, 1H), 2.77 (m, 2H).

IR (KBr): 3303, 3067, 1694, 1538, 1257, 741 cm$^{-1}$.

MS (FD) m/e 329.

Analysis for C$_{32}$H$_{45}$N$_3$O$_4$S: Calcd: C, 65.63; H, 5.81; N, 4.25; Found: C, 65.48; H, 5.82; N, 4.29.

EXAMPLE 1

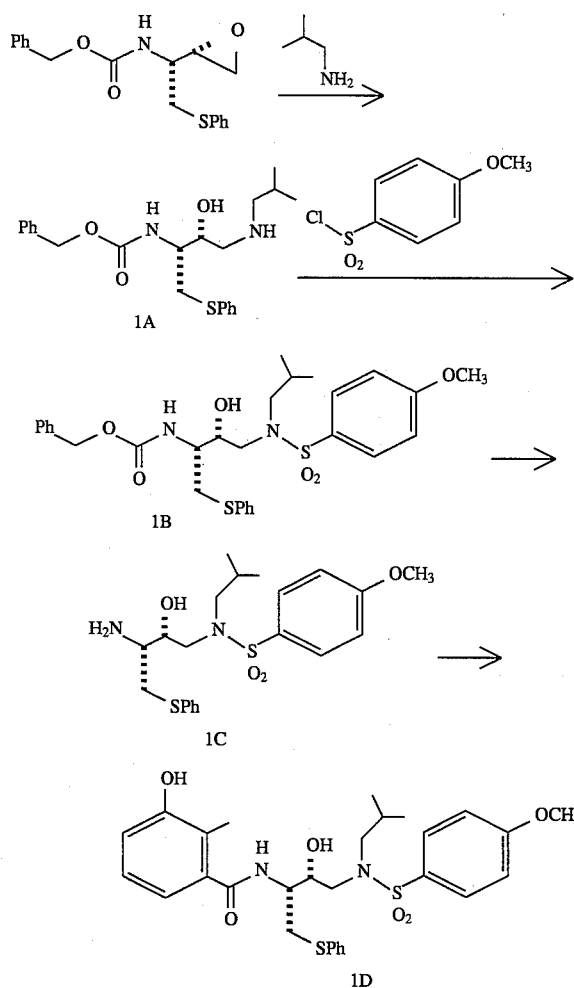

A. Compound 1A

A solution of the titled compound of Preparation 3E and isobutylamine in absolute ethanol are heated at 80° C. overnight. The reaction mixture is reduced to dryness under reduced pressure to provide a residue. This residue is purified using flash chromatography to provide the compound 1A.

B. Compound 1B

To a solution of compound 1A in CH$_2$Cl$_2$ is added excess saturated aqueous sodium bicarbonate solution, sodium bicarbonate, and 4-methoxy benzene sulfonyl chloride. The mixture is stirred vigorously for 24 hours. The resulting mixture is diluted with CH$_2$Cl$_2$, washed with saturated brine, dried over magnesium sulfate and filtered. After concentration of the mixture in vacuo, the residue is purified by flash chromatography to obtain the compound 1B.

C. Compound 1C

A solution of compound 1B in EtOAc is treated at ambient temperature with 10% palladium on carbon and hydrogenated under positive pressure of hydrogen. The mixture is filtered and concentrated in vacuo and the crude residue is purified by flash chromatography to afford compound 1C.

D. Compound 1D

The compound 1C and the compound prepared in Preparation 1, DCC, and HOBT.H$_2$O are mixed together in CH$_2$Cl$_2$ and stirred overnight. The reaction mixture is diluted with CH$_2$Cl$_2$ and washed with H$_2$O. The organics are dried and evaporated to give a residue. The resultant crude material is purified using flash chromatography to provide compound 1D.

EXAMPLE 2

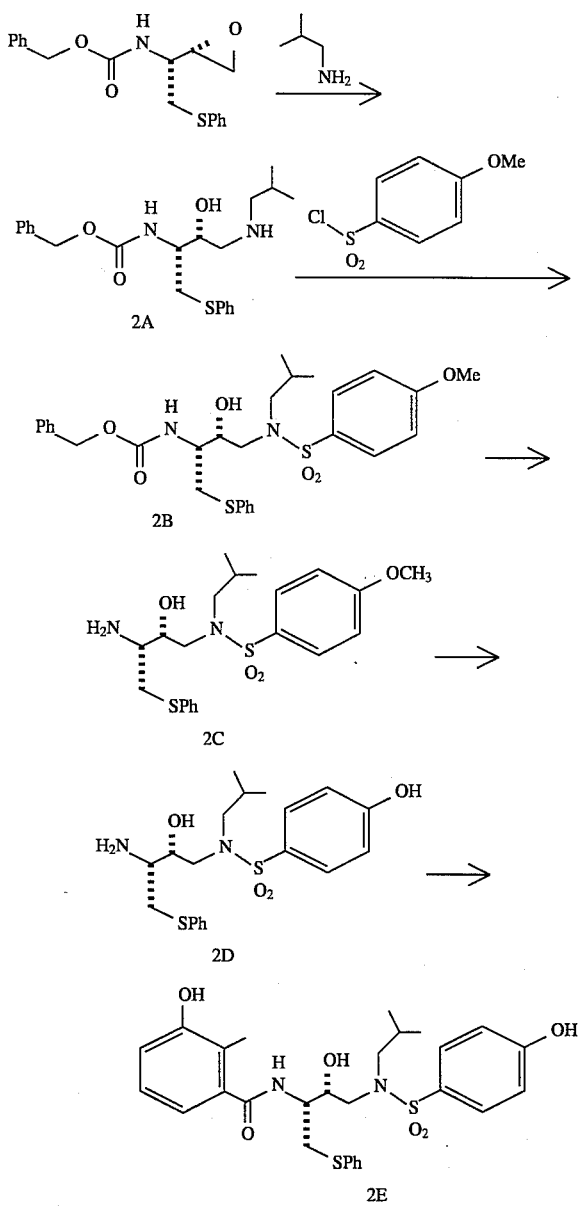

A. Compound 2A

A solution of the titled compound of Preparation 3E and isobutylamine in absolute ethanol are heated at 80° C. overnight. The reaction mixture is reduced to dryness under reduced pressure to provide a residue. This residue is purified using flash chromatography to provide the compound 2A.

B. Compound 2B

To a solution of compound 2A in $CH_2Cl_2$ is added excess saturated aqueous sodium bicarbonate solution, sodium bicarbonate, and 4-methoxy benzene sulfonyl chloride. The mixture is stirred vigorously for 24 hours. The resulting mixture is diluted with $CH_2Cl_2$, washed with saturated brine, dried over magnesium sulfate and filtered. After concentration of the mixture in vacuo, the residue is purified by flash chromatography to obtain the compound 2B.

C. Compound 2C

A solution of compound 2B in EtOAc is treated at ambient temperature with 10% palladium on carbon and hydrogenated under positive pressure of hydrogen. The mixture is filtered and concentrated in vacuo and the crude residue is purified by flash chromatography to afford compound 2C.

D. Compound 2D

A solution of compound 2C in $CH_2Cl_2$ is added to a solution of boron tribromide in $CH_2Cl_2$. The reaction mixture is stirred at ambient temperature for 24 hours. The solution is poured onto a saturated solution of sodium bicarbonate. The aqueous layer is extracted with $CH_2Cl_2$ and EtOAc. The combined organics are dried over anhydrous $MgSO_4$, are concentrated under reduced pressure and the crude product is purified via flash chromatography to afford compound 2D.

E. Compound 2E

The compound 2D and the compound prepared in Preparation 1, DCC, and HOBT.$H_2O$ are mixed together in $CH_2Cl_2$ and stirred overnight. The reaction mixture is diluted with $CH_2Cl_2$ and washed with $H_2O$. The organics are dried and evaporated to give a residue. The resultant crude material is purified using flash chromatography to provide compound 2E.

EXAMPLE 3

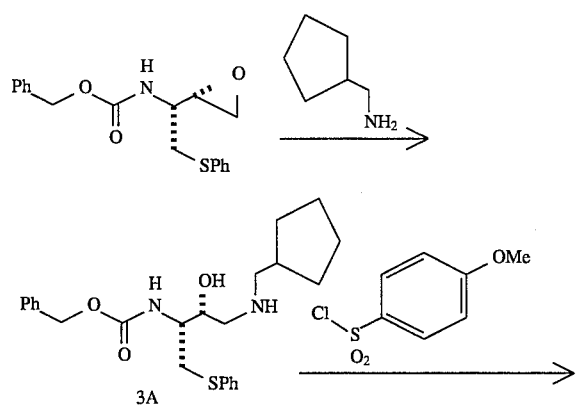

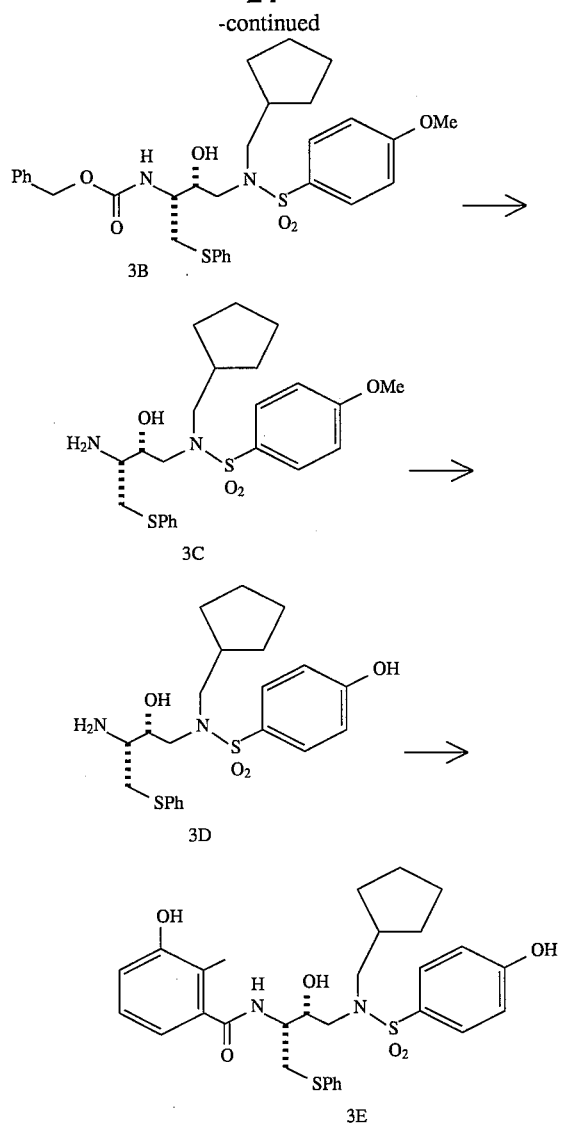

A. Compound 3A

A solution of the titled compound of Preparation 3E and cyclopentylmethylamine in absolute ethanol are heated at 80° C. overnight. The reaction mixture is reduced to dryness under reduced pressure to provide a residue. This residue is purified using flash chromatography to provide the compound 3A.

B. Compound 3B

To a solution of compound 3A in $CH_2Cl_2$ is added excess saturated aqueous sodium bicarbonate solution, sodium bicarbonate, and 4-methoxy benzene sulfonyl chloride. The mixture is stirred vigorously for 24 hours. The resulting mixture is diluted with $CH_2Cl_2$, washed with saturated brine, dried over magnesium sulfate and filtered. After concentration of the mixture in vacuo, the residue is purified by flash chromatography to obtain the compound 3B.

C. Compound 3C

A solution of compound 3B in EtOAc is treated at ambient temperature with 10% palladium on carbon and hydrogenated under positive pressure of hydrogen. The mixture is filtered and concentrated in vacuo and the crude residue is purified by flash chromatography to afford compound 3C.

D. Compound 3D

A solution of compound 3C in CH$_2$Cl$_2$ is added to a solution of boron tribromide in CH$_2$Cl$_2$. The reaction mixture is stirred at ambient temperature for 24 hours. The solution is poured onto a saturated solution of sodium bicarbonate. The aqueous layer is extracted with CH$_2$Cl$_2$ and EtOAc. The combined organics are dried over anhydrous MgSO$_4$, are concentrated under reduced pressure and the crude product is purified via flash chromatography to afford compound 3D.

E. Compound 3E

The compound 3D and the compound prepared in Preparation 1, DCC, and HOBT.H$_2$O are mixed together in CH$_2$Cl$_2$ and stirred overnight. The reaction mixture is diluted with CH$_2$Cl$_2$ and washed with H$_2$O. The organics are dried and evaporated to give a residue. The resultant crude material is purified using flash chromatography to provide compound 3E.

EXAMPLE 4

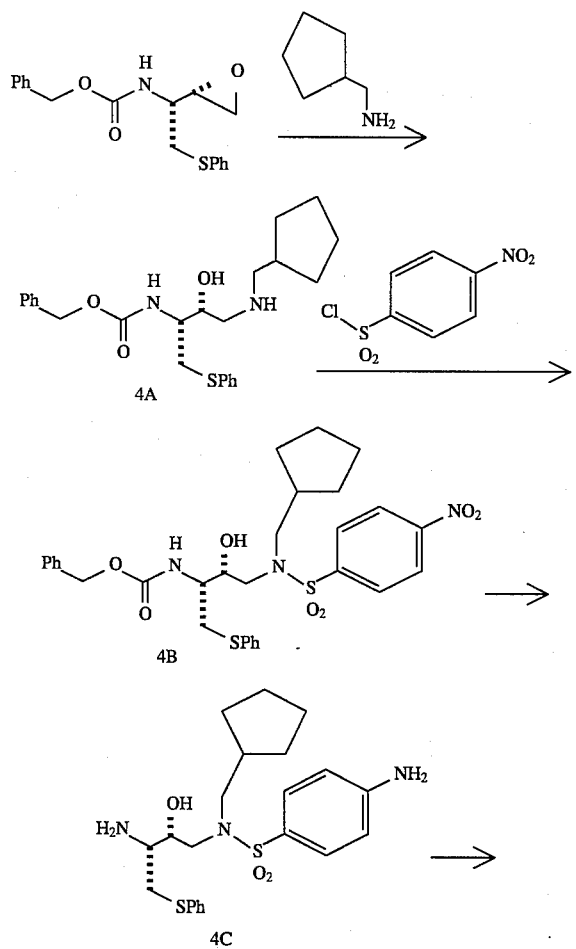

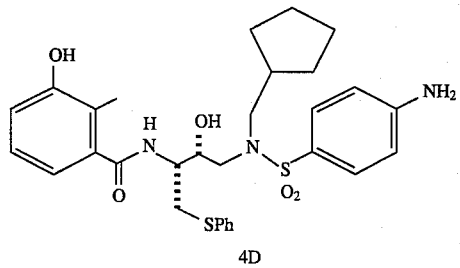

A. Compound 4A

A solution of the titled compound of Preparation 3E and cyclopentylmethylamine in absolute ethanol are heated at 80° C. overnight. The reaction mixture is reduced to dryness under reduced pressure to provide a residue. This residue is purified using flash chromatography to provide the compound 4A.

B. Compound 4B

To a solution of compound 4A in CH$_2$Cl$_2$ is added excess saturated aqueous sodium bicarbonate solution, sodium bicarbonate, and 4-nitro benzene sulfonyl chloride. The mixture is stirred vigorously for 24 hours. The resulting mixture is diluted with CH$_2$Cl$_2$, washed with saturated brine, dried over magnesium sulfate and filtered. After concentration of the mixture in vacuo, the residue is purified by flash chromatography to obtain the compound 4B.

C. Compound 4C

A solution of compound 4B in EtOAc is treated at ambient temperature with 10% palladium on carbon and hydrogenated under positive pressure of hydrogen. The mixture is filtered and concentrated in vacuo and the crude residue is purified by flash chromatography to afford compound 4C.

D. Compound 4D

The compound 4C and the compound prepared in Preparation 1, DCC, and HOBT.H$_2$O are mixed together in CH$_2$Cl$_2$ and stirred overnight. The reaction mixture is diluted with CH$_2$Cl$_2$ and washed with H$_2$O. The organics are dried and evaporated to give a residue. The resultant crude material is purified using flash chromatography to provide compound 4D.

EXAMPLE 5

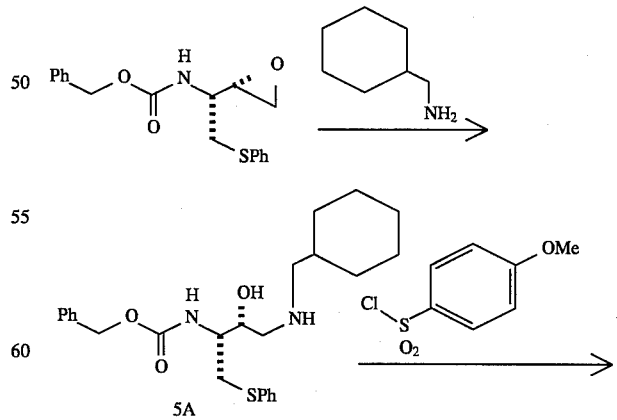

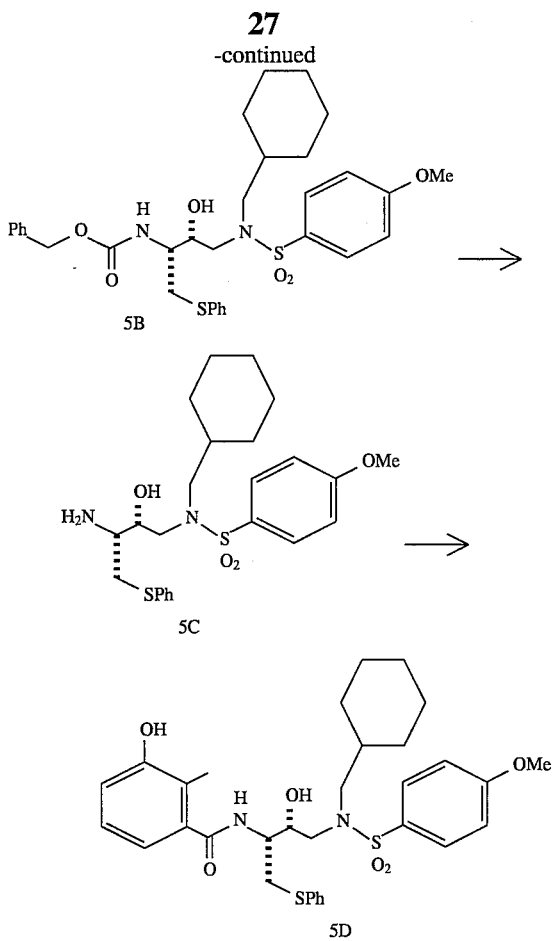

A. Compound 5A

A solution of the titled compound of Preparation 3E and cyclohexylmethylamine in absolute ethanol are heated at 80° C. overnight. The reaction mixture is reduced to dryness under reduced pressure to provide a residue. This residue is purified using flash chromatography to provide the compound 5A.

B. Compound 5B

To a solution of compound 5A in $CH_2Cl_2$ is added excess saturated aqueous sodium bicarbonate solution, sodium bicarbonate, and 4-methoxy benzene sulfonyl chloride. The mixture is stirred vigorously for 24 hours. The resulting mixture is diluted with $CH_2Cl_2$, washed with saturated brine, dried over magnesium sulfate and filtered. After concentration of the mixture in vacuo, the residue is purified by flash chromatography to obtain the compound 5B.

C. Compound 5C

A solution of compound 5B in EtOAc is treated at ambient temperature with 10% palladium on carbon and hydrogenated under positive pressure of hydrogen. The mixture is filtered and concentrated in vacuo and the crude residue is purified by flash chromatography to afford compound 5C.

D. Compound 5D

The compound 5C and the compound prepared in Preparation 1, DCC, and HOBT.$H_2O$ are mixed together in $CH_2Cl_2$ and stirred overnight. The reaction mixture is diluted with $CH_2Cl_2$ and washed with $H_2O$. The organics are dried and evaporated to give a residue. The resultant crude material is purified using flash chromatography to provide compound 5D.

To deprotect a carbobenzyloxy group of a compound in the examples above, e.g., as described in Example 2C, one can reflux the compound in 33% HBr dissolved in acetic acid. After removal of the solvent, the compound is isolated by column chromatography.

As noted above, the compounds of the present invention are useful for inhibiting HIV protease, which is an enzyme associated with viral component production and assembly. An embodiment of the present invention is a method of treating HIV infection comprising administering to a host or patient, such as a primate, an effective amount of a compound of formula (1) or a pharmaceutically acceptable salt thereof. Another embodiment of the present invention is a method of treating AIDS comprising administering to a host or patient an effective amount of a compound of formula (1) or a pharmaceutically acceptable salt thereof. A further embodiment of the present invention is a method of inhibiting HIV protease comprising administering to an HIV infected cell or a host or patient, such as a primate, infected with HIV, an effective amount of a compound of formula (1) or a pharmaceutically acceptable salt thereof.

The term "effective amount" means an amount of a compound of formula (1) or its pharmaceutically acceptable salt that is effective to inhibit the HIV protease mediated viral component production and assembly. The specific dose of compound administered according to this invention to obtain therapeutic or inhibitory effects will, of course, be determined by the particular circumstances surrounding the case, including, for example, the compound administered, the route of administration, the condition being treated and the individual host or patient being treated. An exemplary daily dose (administered in single or divided doses) contains a dosage level of from about 0.01 mg/kg to about 50 mg/kg of body weight of a compound of this invention. Preferred daily doses generally are from about 0.05 mg/kg to about 20 mg/kg and, more preferably, from about 0.1 mg/kg to about 10 mg/kg.

The compounds of the invention may be administered by a variety of routes, including oral, rectal, transdermal, subcutaneous, intravenous, intramuscular and intranasal routes. The compounds of the present invention are preferably formulated prior to administration. Therefore, another embodiment of the present invention is a pharmaceutical composition or formulation comprising an effective amount of a compound of formula (1) or a pharmaceutically acceptable salt thereof and a pharmaceutically acceptable carrier, such as a diluent or excipient therefor.

The active ingredient preferably comprises from 0.1% to 99.9% by weight of the formulation. By "pharmaceutically acceptable" it is meant that the carrier, such as the diluent or excipient, is compatible with the other ingredients of the formulation and not deleterious to the host or patient.

Pharmaceutical formulations may be prepared from the compounds of the invention by known procedures using known and readily available ingredients. Examples of such ingredients include, but are not limited to, avicel, starch, lactose, calcium sulphate dihydrate, terra alba, sucrose, talc, gelatin, agar, pectin, acacia, magnesium stearate, stearic acid, peanut oil, olive oil, glyceryl monostearate, Tween 80, 1,3-butanediol, cocoa butter, beeswax, polyethylene glycol, propylene glycol, sorbitan monostearate, polysorbate 60, cetearyl alcohol, 2-octyldodecanol, benzyl alcohol, glycine, sorbic acid, potassium sorbate, disodium hydrogen phosphate, sodium chloride, and water. In making the compositions of the present invention, the active ingredient will usually be admixed with a carrier, or diluted by a carrier, or enclosed within a carrier, which may be in the form of a capsule, sachet, paper or other suitable container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments (containing, for example, up to 10% by weight of the active compound), soft and hard gelatin capsules, suppositories, sterile injectable solutions, sterile packaged powders and the like.

ACTIVITY SCREENING

A number of tests can be used to test the biological activity of HIV protease inhibitory compounds. For example, tests can be used to analyze proteolytic inhibition rates and antiviral effects on HIV-infected cell lines. The procedures for some of these experiments are described below.

I. IC50 and $K_i$ Determination of Anti-HIV Coumpounds

Proteolytic activity of purified HIV-1 protease is routinely measured using the chromogenic assay developed by Richards et al. (J. Biol. Chem. 265: 7733 (1990)). Synthetic peptide His-Lys-Ala-Arg-Val-Leu-Phe (pNO2))-Glu-Ala-Nle-Ser-NH2 (American Peptide Company) is used as the substrate.

The assay is carried out in 0.5M NaCl, 50 mM MES pH 5.6, 2% DMSO (dimethylsulfoxide) at 37° C. Cleavage of the scissile bond between leucine and paranitrophenylalanine (Phe(pNO2)) is assayed by spectrophotometric monitoring of the decrease in absorbance at 305 nm. Initial velocity is determined as the rate of decline of absorbance during the first 100 seconds of reaction. Under standard conditions, the Michaelis constant (Km) for this substrate is 52±16 µM.

For determination of inhibition rates of HIV-1 protease inhibitors, saturated concentration of substrate (200 µM) is used. Between 15–25 concentrations of inhibitor are added and velocity of reaction is measured at each of the concentrations, as described above.

Inhibition constants are calculated using the method of Jackson et al. (Adv. in Enzyme Regulation 22: 187 (1984)). In the above described assay, Pepstatin A-a standard inhibitor of aspartic proteases has a Ki app=3.1±0.1 µM and $IC_{50}$=3.8±0.7 µM.INSERT GLENN'S SECTION FROM AGOU116.

II. Primary Drug Screening of Anti-HIV Compounds at Southern Research Institute (SRI)

A. Principle of MTT Assay:

SRI has an established program for the primary antiviral analysis of compounds in microtiter assays which measures the ability of a selected compound to inhibit HIV-induced cell killing. This assay involves the conversion of the tetrazolium dye MTT to a colored formazan product by mitochondrial enzymes in metabolically active cells. This assay system is used at SRI to screen over 30,000 compounds per year. Briefly, the assay involves the infection of CEM or MT2 cells in round bottom 96-well plates. The compound of interest is added just prior to infection. Following 6 days of incubation at 37° C. the plates are stained with MTT. The results of the assay are quantitated spectrophotometrically on a Molecular Devices Vmax plate reader. The data are analyzed by linear regression utilizing an in-house software program to calculate antiviral activity ($IC_{25}$, $IC_{50}$, $IC_{95}$) and toxicity ($TC_{25}$, $TC_{50}$, $TC_{95}$) as well as other values.

Primary antiviral assays are routinely performed in CEM or MT-2 cells. SRI has found that all active compounds have been identified in CEM cells, while experiments performed in the MT-2 cell line miss a small proportion of the active compounds.

B. Standard Screening Assays in CEM and MT-2 Cells

1. Compound dilution and delivery to the plates

Compounds are solubilized in the appropriate vehicle such as distilled water or DMSO if necessary. Latex gloves, lab coats and masks are used during all phases of the handling process to prevent exposure to potentially harmful agents. The drug is prepared at the appropriate concentration and stored at −20° C. until used by the screening laboratory. The first dilution of each compound is made in a dilution tube with medium to yield a concentration two-fold that of the highest test concentration. Sterile titer tubes are then used to make serial one half-log dilutions of each compound. Following drug dilution, the diluted compound is added to the appropriate well of a 96-well microtiter plate. Up to 12 dilutions can be assayed conveniently in triplicate on a single plate with all appropriate controls including cell control, virus control, toxicity control, drug color control, medium control and plastic (background) control. When testing includes only six dilutions, two drugs can be assayed on a single microtiter plate. The drugs are added to the plate in a final volume of 100 microliters.

2. Cells and virus

During the time the drug dilutions are prepared, cells are washed and counted. Viability is monitored by trypan blue dye exclusion and assays are not performed if the viability falls below 90%. Cells are maintained in an exponential growth phase and are split 1:2 on the day prior to assay to assure exponential growth rate.

For the primary screen, the cell lines utilized are CEM and MT-2. Unless otherwise indicated, the medium used is RPMI 1640 with 10% heat-inactivated fetal calf serum (FBS), glutamine and antibiotics.

Cells are propagated at 37° C. in an atmosphere of 5% $CO_2$ in air. The virus employed for this work is HIV-1 isolates IIIB and/or RF, which are prepared by an acute infection process.

Briefly, virus-infected cells are pelleted on a daily basis beginning at three days post-infection until the virus has killed all of the cells in the culture. Reverse transcriptase activity and p24 ELISA are used to identify pools with the greatest amount of virus.

These 24-hour harvests are pooled, filtered and frozen at −90° C. Prior to use in the assay, the infectious pool of virus is titered on all available cell lines in order to determine the amount of virus required in the antiviral assay.

In general, pools produced by the acute infection method require the addition of one microliter of infectious virus per well resulting in the screening of drugs at a multiplicity of infection of 0.01. In this manner, enough virus is prepared and frozen to complete over one thousand microtiter plates, allowing the testing of up to two thousand compounds from a single stock of infectious virus. The use of a single stock of virus for a long period of testing has very favorable effects on the repeatability of the assay systems.

Virus infection of the CEM and MT-2 cells for the antiviral assay is carried out in a bulk infection process. The appropriate number of cells required to complete the assay is mixed with infectious virus in a conical centrifuge tube in a small total volume of 1–2 milliliters.

Following a 4-hour incubation the infected cells are brought to the appropriate final concentration of $5\times10^4$ cells per milliliter with fresh tissue culture medium and 100 microliters are added to the appropriate experimental and virus control wells. Uninfected cells at the same concentration are plated for the toxicity controls and for the cell controls. Assays can also be performed using an in-well infection method. In this case, drug, cells and virus are added to the well individually. In each case the MOI is adjusted to give complete cell killing in the virus control wells by Day 6.

3. Evaluation of CPE-inhibition

Following the addition of cells and drugs to the microtiter plate, the plate is incubated for 6 days at 37° C. Experience has determined that incubation for longer periods of time (7–8 days) or the use of higher input cell numbers ($1\times10^4$) results in significant decreases in cell control viability and a narrowing in the differential in optical density between cell and virus controls upon staining with MTT.

The method of evaluating the antiviral assay involves the addition of 20 microliters of the tetrazolium salt MTT at 5 mg/ml to each well of the plate for 4–8 hours. After this incubation period, the cells are disrupted by the addition of 50 microliters of 20% SDS in 0.01N HCl.

The metabolic activity of the viable cells in the culture result in a colored reaction product which is measured spectrophotometrically in a Molecular Devices Vmax plate reader at 570 nm. The optical density (O.D.) value is a function of the amount of formazan product which is proportional to the number of viable cells.

The plate reader is on-line to the screening laboratory microcomputer which evaluates the plate data and calculates plate data. The plate report provides a rundown of all pertinent information including the raw O.D. values, the calculated mean O.D.'s and the percent reduction in viral CPE as well as calculations including $TC_{50}$, $IC_{50}$ and antiviral and specificity indices. Finally, the results include a plot which visually depicts the effect of the compound on uninfected cells (toxicity) and the protective or nonprotective effect of the compound on the infected cells.

Numerous examples of compounds according to the present invention are contained in Appendix I, which is attached. Appendix I contains options for Q1, and Q2, and the left side of Formula 1. Any combination of these components may be made, and the invention is not limited to the options shown.

APPENDIX I $Q_1$ can be chosen from, but is not limited to:

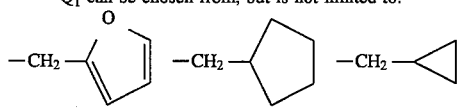

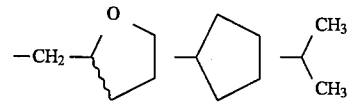

APPENDIX I-continued

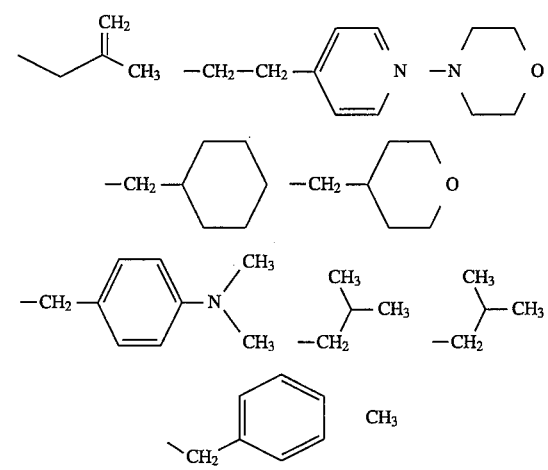

$Q_2$ can be chosen from, but is not limited to:

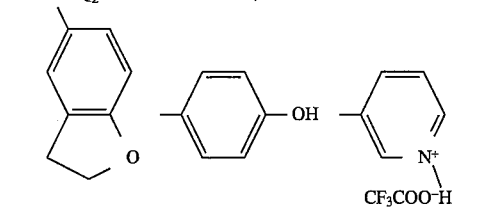

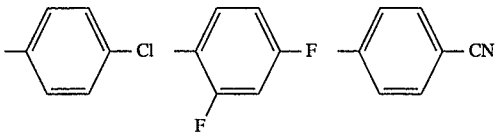

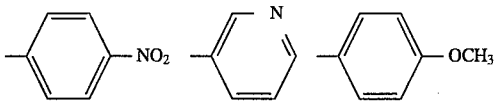

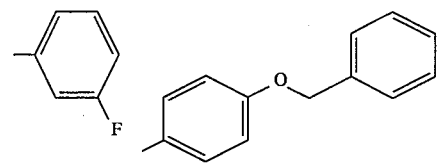

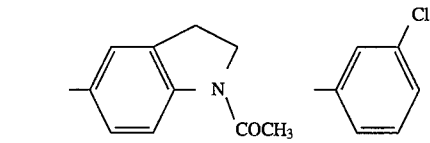

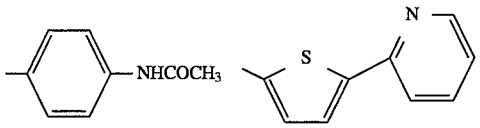

APPENDIX I-continued
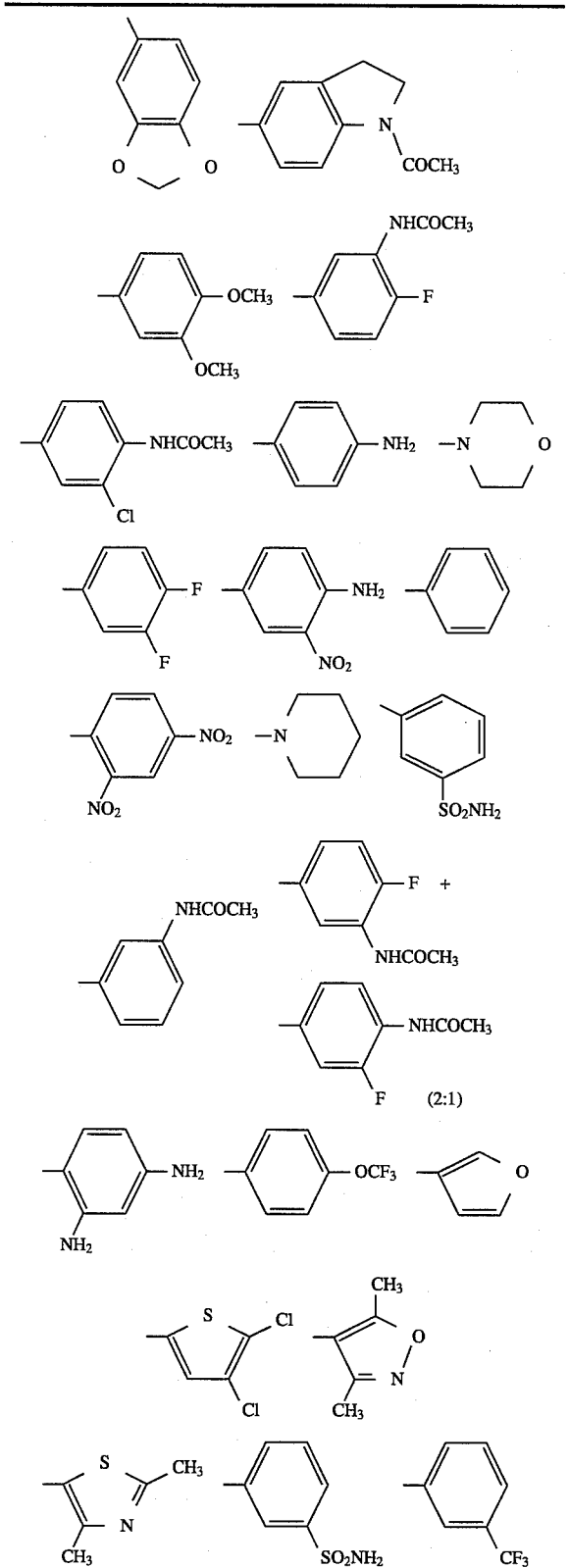
APPENDIX I-continued
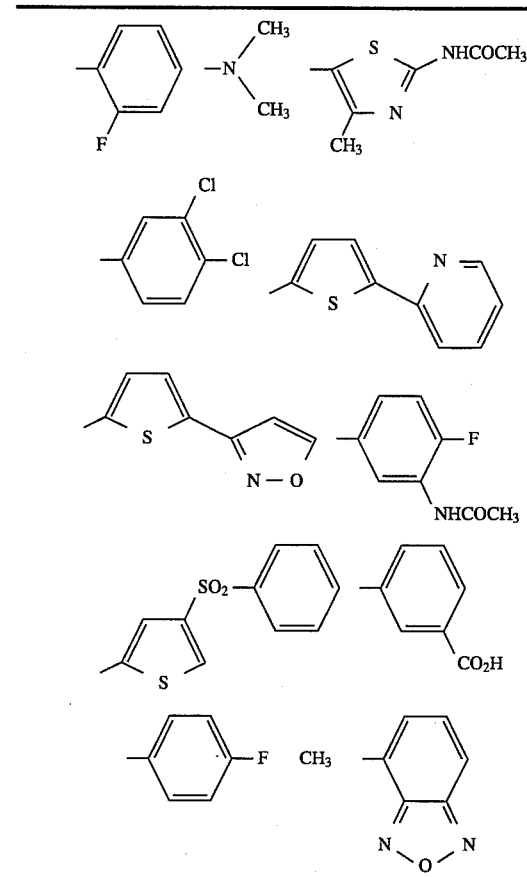
EXAMPLES FOR THE LEFT PORTION OF
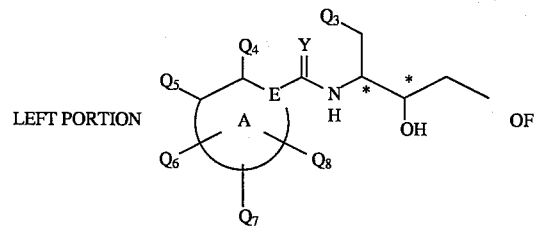
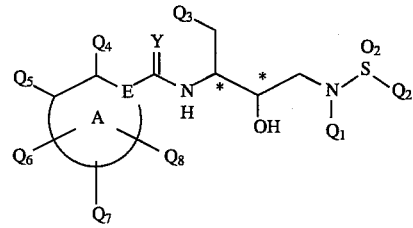
FORMULA 1
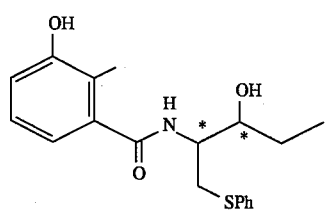

APPENDIX I-continued

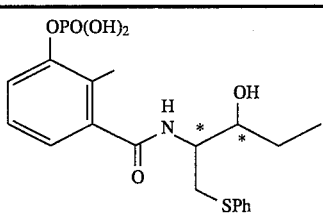

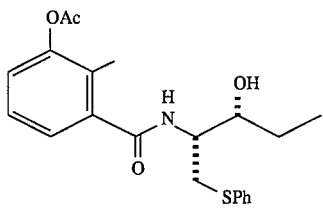

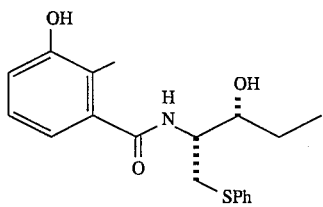

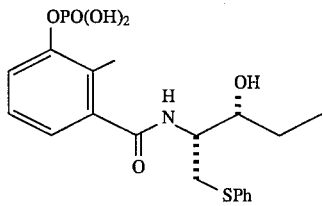

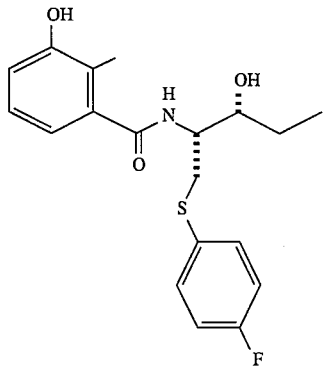

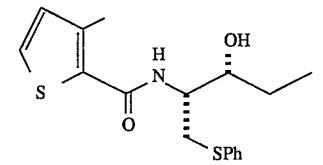

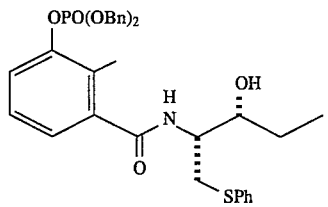

APPENDIX I-continued

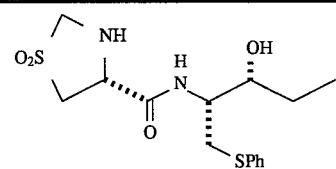

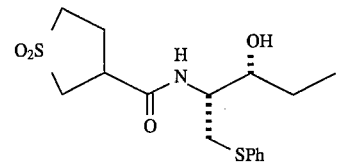

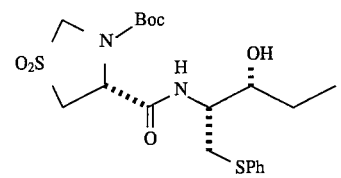

What is claimed is:
1. A compound of the formula (1)

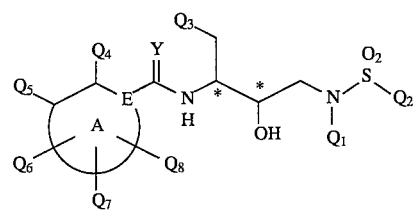

(1)

wherein:

$Q_1$ is selected from substituted and unsubstituted carbocycle, heterocycle, alkyl, alkynyl, and alkenyl;

$Q_2$ is selected from hydroxyl, halogen, hydrolyzable group, and substituted and unsubstituted carbocycle, heterocycle, alkyl, alkoxyl, carbocyclyloxyl, heterocyclyloxyl, amino, acyl, alkynyl, and alkenyl;

$Q_3$ is selected from mercapto, substituted aryl and aryloxyl, and substituted and unsubstituted thioether, amino, and partially saturated heterocyle;

$Q_4$–$Q_8$, when present, are independently selected from hydrogen, dioxide, hydroxyl, mercapto, nitro, halogen, —O—J wherein J is a substituted or unsubstituted hydrolyzable group, and substituted and unsubstituted alkoxyl, aryloxyl, thioether, acyl, sulfinyl, sulfonyl, amino, alkyl, cycloalkyl, alkenyl, alkynyl, saturated and partially saturated heterocycle and aryl, and further wherein any one or more of $Q_4$–$Q_8$ may be a member of a spiro ring and any two of $Q_4$–$Q_8$ may be members of the same ring;

Y is selected from oxygen, —N—H, —N-alkyl, —N-alkenyl, —N-alkynyl, sulfur, selenium, and two hydrogen atoms;

E is carbon or nitrogen; and

A is a carbocycle or heterocycle, which is optionally further substituted;

or a pharmaceutically acceptable salt thereof.

2. A compound or salt of claim 1, wherein:

$Q_1$ is selected from substituted and unsubstituted aryl, cycloalkyl, $C_{1-6}$ alkyl and $C_{2-4}$ alkenyl;

$Q_2$ is selected from hydroxyl, halogen, hydrolyzable group, and substituted and unsubstituted aryl, alkyl, cycloalkyl, alkoxyl, aryloxyl, amino and alkenyl;

$Q_3$ is selected from mercapto and substituted and unsubstituted thioether and amino;

$Q_4$–$Q_8$, when present, are independently selected from hydrogen, hydroxyl, halogen, —O—J wherein J is a substituted or unsubstituted hydrolyzable group, and substituted and unsubstituted acyl, alkoxyl, amino and alkyl, and further wherein any two or more of $Q_4$–$Q_8$ may form part of a ring;

Y is oxygen; and

A is a monocyclic carbocycle or heterocycle.

3. A compound or salt of claim 2, wherein:

the substituents for the $C_{1-6}$ alkyl and $C_{2-4}$ alkenyl groups of $Q_1$ are independently selected from hydroxyl and substituted and unsubstituted carbocycle, heterocycle, aryloxyl and alkoxyl; the substituents for the cycloalkyl group of $Q_1$ are selected from aryl, and the cycloalkyl group is optionally fused to the aryl group; and the substituents for the aryl group of $Q_1$ are selected from hydroxyl; alkoxyl optionally substituted with aryl; alkyl optionally substituted with hydroxyl, alkoxyl, aryloxyl, cycloalkyl or aryl; aryloxyl; and aryl; and the substituents for the aryl, cycloalkyl and aryloxyl groups of $Q_2$ are selected from hydroxyl; halo; —$CF_3$; —CN; —N(H)—C(O)H; alkyl optionally substituted with one or more substituents selected from hydroxyl and substituted and unsubstituted aryl; acyl; —$CO_2$-alkyl optionally substituted with one or more substituents selected from hydroxyl and substituted and unsubstituted aryl; and substituted and unsubstituted alkoxyl, amino and —N(alkyl)—C(O)-alkyl.

4. A compound or salt of claim 3, wherein:

the alkoxyl substituent for the $C_{1-6}$ alkyl group and for the alkyl group of $Q_1$ is optionally substituted with aryl; and the substituents for the aryl, cycloalkyl and aryloxy groups of $Q_2$ are selected from hydroxyl and substituted and unsubstituted alkoxyl and amino.

5. A compound or salt of claim 3, wherein:

$Q_1$ is $C_{1-6}$ alkyl optionally substituted with substituted or unsubstituted carbocycle or heterocycle;

$Q_2$ is selected from substituted and unsubstituted aryl and cycloalkyl, which said aryl and cycloalkyl are optionally substituted with one or more substituents selected from hydroxyl and substituted and unsubstituted alkoxyl and amino;

$Q_3$ is selected from substituted and unsubstituted —S-aryl;

$Q_4$ is substituted or unsubstituted alkyl;

$Q_5$ is hydroxyl, —O—J wherein J is a hydrolyzable group, or substituted or unsubstituted alkoxyl or amino;

E is carbon; and

A is a carbocycle that is an aromatic 5–14 membered monocyclic or polycyclic ring or a heterocycle that is an aromatic or a saturated or partially saturated 5–7 membered monocyclic ring having from one to three heteroatoms selected from nitrogen, oxygen and sulfur, and A is optionally further substituted.

6. A compound or salt of claim 5, wherein:

$Q_1$ is $C_{1-4}$ alkyl optionally substituted with an unsubstituted carbocycle or heterocycle;

$Q_2$ is selected from substituted and unsubstituted aryl;

$Q_3$ is unsubstituted —S-aryl;

$Q_4$ is unsubstituted $C_{1-6}$ alkyl;

$Q_5$ is hydroxyl, amino, or O—J wherein J is a substituted or unsubstituted hydrolyzable group;

$Q_6$, $Q_7$ and $Q_8$ are each hydrogen; and

A is a carbocycle that is an aromatic 5–7 membered monocyclic ring or a heterocycle that is an aromatic or a saturated or partially saturated 5–6 membered monocyclic ring having from one to three heteroatoms selected from nitrogen, oxygen and sulfur, and A is optionally further substituted.

7. A compound or salt of claim 6, wherein:

$Q_1$ is $C_{1-4}$ alkyl optionally substituted with an unsubstituted carbocycle;

$Q_2$ is a substituted carbocyclic aromatic 5–14 membered monocyclic ring;

$Q_3$ is unsubstituted thiophenyl or thionaphthyl;

$Q_4$ is methyl;

$Q_5$ is hydroxyl or O—J; and

A is phenyl or a heterocycle that is an aromatic or a saturated or partially saturated 5–6 membered monocyclic ring having from one to two heteroatoms selected from nitrogen and sulfur, and A is optionally further substituted.

8. A compound or salt of claim 7, wherein:

$Q_1$ is $C_{1-4}$ alkyl optionally substituted with an unsubstituted cycloalkyl;

$Q_2$ is a carbocyclic aromatic 5–7 membered monocylic ring substituted with at least one group selected from hydroxyl, unsubstituted alkoxyl and —$NH_2$;

$Q_3$ is unsubstituted thiophenyl;

$Q_5$ is hydroxy, —O-acetyl or —$OPO(OH)_2$; and

A is phenyl or a heterocycle that is an aromatic or a saturated or partially saturated 5–6 membered monocyclic ring having from one to two heteroatoms selected from nitrogen and sulfur, and A is optionally further substituted.

9. A compound or salt of claim 8, wherein:

$Q_1$ is $C_{1-4}$ alkyl optionally substituted with an unsubstituted 5–7 membered monocyclic cycloalkyl ring;

$Q_2$ is phenyl substituted with at least one group selected from hydroxyl, unsubstituted alkoxyl and —$NH_2$; and A is phenyl or a heterocycle that is an aromatic or a saturated or partially saturated 5–6 membered monocyclic ring having from one to two heteroatoms selected from nitrogen and sulfur.

10. A compound or salt of claim 1, wherein:

$Q_1$ is $C_{1-4}$ alkyl optionally substituted with an unsubstituted saturated 5–7 membered monocyclic cycloalkyl ring;

$Q_2$ is phenyl substituted at the position para to the —$SO_2$ group of formula (1) with a member selected from hydroxyl, unsubstituted alkoxyl and —$NH_2$;

$Q_3$ is substituted or unsubstituted phenyl or thiophenyl;

Y is oxygen;

E is carbon; and

A is phenyl, tetrahydrothiazole, thienyl or tetrahydrothienyl.

11. A compound or salt of claim 10, wherein:

$Q_1$ is $C_{1-4}$ alkyl optionally substituted with an unsubstituted saturated 5–6 membered monocyclic cycloalkyl ring; and $Q_2$ is phenyl substituted at the position para to said —$SO_2$ group with an unsubstituted $C_{1-3}$ alkoxyl.

12. A compound or salt of claim 11, wherein:

$Q_1$ is substituted or unsubstituted methyl or isobutyl; and $Q_2$ is phenyl substituted at the position para to said —$SO_2$ group with unsubstituted methoxyl.

13. A compound or salt of claim 12, wherein:

$Q_1$ is methyl substituted with cyclopentyl or cyclohexyl.

14. A compound or salt of claim 2, wherein:

$Q_1$ is $C_{1-4}$ alkyl optionally substituted with hydroxyl or substituted or unsubstituted cycloalkyl, aryloxyl, alkoxyl or aryl.

15. A compound or salt of claim 2, wherein:

$Q_1$ is $C_{1-3}$ alkyl or $C_3$ alkenyl optionally substituted with hydroxyl or substituted or unsubstituted cycloalkyl, aryloxyl, alkoxyl or aryl.

16. A compound of the formula (1)

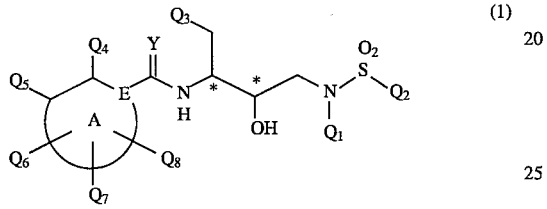

wherein:

$Q_1$ is selected from G; $C_1$–$C_4$ alkyl optionally substituted with one or more groups selected from $C_3$–$C_6$ cycloalkyl, —$OR^2$, —$R^3$, —O—G and G; $C_2$–$C_4$ alkenyl optionally substituted with one or more groups selected from $C_3$–$C_6$ cycloalkyl, —$OR^2$, —$R^3$, —O—G and G; $C_3$–$C_6$ cycloalkyl optionally substituted with or fused with G;

$Q_2$ is selected from $D_2$; O—$D_2$; $D_2$—$D_2$; —O—$R^3$; —$NR^2R^3$; $C_1$–$C_6$ alkyl optionally substituted with one or more groups selected from $R^4$ and $D_2$; $C_2$–$C_6$ alkenyl optionally substituted with one or more groups selected from $R^4$ and $D_2$; $C_3$–$C_6$ saturated carbocycle optionally substituted with one or more groups selected from $R^4$ and $D_2$; and $C_5$–$C_6$ unsaturated carbocycle optionally substituted with one or more groups selected from $R^4$ and $D_2$;

$Q_3$ is selected from mercapto, substituted aryl and aryloxyl, and substituted and unsubstituted thioether, amino and partially saturated heterocycle;

$Q_{4-8}$, when present, are independently selected from hydrogen, hydroxyl, mercapto, nitro, halogen, —O—J wherein J is a substituted or unsubstituted hydrolyzable group, and substituted and unsubstituted alkoxyl, aryloxyl, thioether, acyl, sulfinyl, sulfonyl, amino, alkyl, cycloalkyl, alkenyl, alkynyl, saturated and partially saturated heterocycle and aryl, and further wherein any one or more of $Q_4$–$Q_8$ may be a member of a spiro ring and any two of $Q_4$–$Q_8$ may be members of the same ring;

Y is selected from oxygen, —N—H, —N-alkyl, —N-alkenyl, —N-alkynyl, sulfur, selenium and two hydrogen atoms;

E is carbon or nitrogen; and

A is a carbocycle or heterocycle, and is optionally further substituted;

where:

each G is independently selected from saturated and unsaturated 3–6 membered carbocycle and saturated and unsaturated 5–6 membered heterocycle having one or more heteroatoms selected from O, N, S, $S(O)_n$ and $N(R^2)$, which said carbocycle and heterocycle are optionally substituted with one or more groups selected from oxo, —$OR^2$, —$R^2$, —$N(R^2)(R^2)$, —$N(R^2)$—C(O)—$R^2$, —$R^2$—OH, —CN, —$CO_2R^2$, —C(O)—$N(R^2)(R^2)$, halo and —$CF_3$;

each $R^2$ is independently selected from hydrogen and $C_1$–$C_3$ alkyl optionally substituted with G;

each $R^3$ is independently selected from hydrogen, $D_2$, $C_1$–$C_6$ alkyl, $C_2$–$C_6$ alkenyl, $C_3$–$C_6$ cycloalkyl and $C_5$–$C_6$ cycloalkenyl, wherein when $R^3$ is other than hydrogen, $R^3$ is optionally substituted with one or more substituents selected from —$OR^2$, —C(O)—NH—$R^2$, —$S(O)_n$—$N(R^2)(R^2)$, $D_2$, —CN, —$SR^2$, —$CO_2R^2$ and $NR^2$—C(O)—$R^2$;

each $R^4$ is independently selected from —$OR^2$, —C(O)—$NHR^2$, —$S(O)_2$—$NHR^2$, halo, —$NR^2$—C(O)—$R^2$ and —CN;

each n is independently 1 or 2; and each $D_2$ is independently selected from $C_3$–$C_7$ cycloalkyl, $C_5$–$C_7$ cycloalkenyl, $C_6$–$C_{10}$ aryl, and 5–7 membered saturated and unsaturated heterocycle having one or more heteroatoms selected from N, $N(R^2)$, O, S and $S(O)_n$, wherein said heterocycle is optionally benzofused; and $D_2$ is optionally substituted with one or more substituents selected from oxo, —$OR^2$, —$R^2$, —$N(R^2)(R^2)$, —$R^2$—OH, —CN, —$CO_2R^2$, C(O)—$N(R^2)(R^2)$, —$S(O)_2$—$N(R^2)(R^2)$, —$N(R^2)$—C(O)—$R^2$, —C(O)—$R^2$, —$S(O)_n(R^2)$, —$OCF_3$, —$S(O)_n$—G, methylenedioxy, —$N(R^2)$—$S(O)_2(R^2)$, halo, —$CF_3$, —$NO_2$, G and —O—G;

or a pharmaceutically acceptable salt thereof.

17. A compound or salt of claim 16, wherein:

$Q_1$ is $C_1$–$C_4$ alkyl optionally substituted with $C_3$–$C_6$ cycloalkyl or G;

$Q_2$ is $C_3$–$C_7$ cycloalkyl, $C_5$–$C_7$ cycloalkenyl or $C_6$–$C_{10}$ aryl, each of which is optionally substituted with one or more substituents selected from oxo, —$OR^2$, —$R^2$, —$N(R^2)(R^2)$, —$R^2$—OH, —CN, —$CO_2R^2$, —C(O)—$N(R^2)(R^2)$, —$S(O)_2$—$N(R^2)(R^2)$, —$N(R^2)$—C(O)—$R^2$, —C(O)—$R^2$, —$S(O)_n(R^2)$, —$OCF_3$, —$S(O)_n$—G, methylenedioxy, —$N(R^2)$—$S(O)_2(R^2)$, halo, —$CF_3$, —$NO_2$, G and —O—G;

$Q_3$ is selected from mercapto and substituted and unsubstituted thioether and amino;

$Q_{4-8}$, when present, are selected from hydrogen, hydroxyl, halogen, —O—J wherein J is a substituted or unsubstituted hydrolyzable group, and substituted and unsubstituted acyl, alkoxyl, amino and alkyl, and further wherein any two or more of $Q_4$–$Q_8$ may form part of a ring;

Y is oxygen; and

A is a monocyclic carbocycle or heterocycle.

18. A compound or salt of claim 17, wherein:

$Q_1$ is $C_1$–$C_4$ alkyl optionally substituted with $C_3$–$C_6$ cycloalkyl;

$Q_2$ is $C_6$–$C_{10}$ aryl optionally substituted with one or more substituents selected from oxo —$OR^2$, —$R^2$, —$N(R^2)(R^2)$, —$R^2$—OH, —CN, —$CO_2R^2$, —C(O)—$N(R^2)(R^2)$, —$S(O)_2$—$N(R^2)(R^2)$, —$N(R^2)$—C(O)—$R^2$, —C(O)—$R^2$, —$S(O)_n(R^2)$, —$OCF_3$, —$S(O)_n$—G, methylenedioxy, —$N(R^2)$—$S(O)_2(R^2)$, halo, —$CF_3$, —$NO_2$, G and —O—G;

$Q_3$ is selected from substituted and unsubstituted —S-aryl;

$Q_4$ is substituted or unsubstituted alkyl;

$Q_5$ is hydroxyl, —O—J wherein J is a hydrolyzable group, or substituted or unsubstituted alkoxyl or amino;

E is carbon; and

A is monocyclic aromatic 5–7 membered ring wherein all the ring members are carbon atoms, or a monocyclic aromatic or a saturated or partially saturated 5–7 membered ring having from one to three heteroatoms selected from nitrogen, oxygen and sulfur.

19. A compound or salt of claim 18, wherein:

$Q_1$ is $C_{1-4}$ alkyl optionally substituted with $C_3$–$C_6$ cycloalkyl;

$Q_2$ is $C_6$–$C_{10}$ aryl optionally substituted with one or more substituents selected from —$OR^2$ and —$N(R^2)(R^2)$;

$Q_3$ is unsubstituted —S-aryl;

$Q_4$ is unsubstituted $C_{1-6}$ alkyl;

$Q_5$ is hydroxyl, amino, or O—J wherein J is a substituted or unsubstituted hydrolyzable group;

$Q_6$, $Q_7$ and $Q_8$ are each hydrogen; and

A is an aromatic 5–6 membered monocyclic ring wherein all the ring members are carbon atoms, or an aromatic or a saturated or partially saturated 5–6 membered monocyclic ring having from one to three heteroatoms selected from nitrogen, oxygen and sulfur.

20. A compound or salt of claim 19, wherein:

$Q_1$ is unsubstituted isobutyl or methyl optionally substituted with $C_5$–$C_6$ cycloalkyl;

$Q_2$ is $C_6$ aryl optionally substituted with one or more substituents selected from —$OR^2$ and —$N(R^2)(R^2)$;

$Q_3$ is unsubstituted thiophenyl or thionaphthyl;

$Q_4$ is methyl;

$Q_5$ is hydroxyl or O—J; and

A is phenyl, or an aromatic or a saturated or partially saturated 5–6 membered monocyclic ring having from one to two heteroatoms selected from nitrogen and sulfur;

where:

each $R^2$ is independently hydrogen or $C_1$–$C_3$ alkyl.

21. A compound or salt of claim 20, wherein:

$Q_3$ is unsubstituted thiophenyl; and $Q_5$ is hydroxy, —O-acetyl or —$OPO(OH)_2$.

22. A compound or salt of claim 21, wherein:

A is phenyl or a monocyclic aromatic or a saturated or partially saturated 5–6 membered ring having from one to two heteroatoms selected from nitrogen and sulfur.

23. A compound or salt of claim 22, wherein:

A is phenyl, thiazolinoyldioxide, thienoyl or tetrahydrothienoyldioxide.

24. A compound of the formula (1)

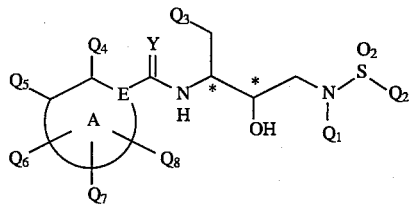

wherein:

$Q_1$ is selected from G; alkyl optionally substituted with one or more groups selected from cycloalkyl —$OR^2$, —$R^3$, —O—G and G; alkenyl optionally substituted with one or more groups selected from cycloalkyl, —$OR^2$, —$R^3$, —O—G and G; and cycloalkyl optionally substituted with or fused with G;

each G is independently selected from saturated and unsaturated carbocycle and saturated and unsaturated heterocycle having one or more heteroatoms selected from O, N, S, $S(O)_n$ and $N(R^2)$, which said carbocycle and heterocycle are optionally substituted with one or more groups selected from oxo, —$OR^2$, —$R^2$, —$N(R^2)(R^2)$, —$N(R^2)$—C(O)—$R^2$, —$R^2$—OH, —CN, —$CO_2R^2$, —C(O)—$N(R^2)(R^2)$, halo and —$CF_3$;

each R is independently selected from hydrogen and alkyl optionally substituted with G;

each $R^3$ is independently selected from hydrogen, $D_2$, alkyl, alkenyl, cycloalkyl and cycloalkenyl, wherein when $R^3$ is other than hydrogen, $R^3$ is optionally substituted with one or more substituents selected from —$OR^2$, —C(O)—NH—$R^2$, —$S(O)_n$—$N(R^2)(R^2)$, $D_2$, —CN, —$SR^2$, —$CO_2R^2$ and $NR^2$—C(O)—$R^2$;

each n is independently 1 or 2;

each $D_2$ is independently selected from cycloalkyl, cycloalkenyl, aryl, and saturated and unsaturated heterocycle having one or more heteroatoms selected from N, $N(R^2)$, O, S and $S(O)_n$, wherein said heterocycle is optionally benzofused; and $D_2$ is optionally substituted with one or more substituents selected from oxo, —$OR^2$, —$R^2$, —$N(R^2)(R^2)$, —$R^2$—OH, —CN, —$CO_2R^2$, —C(O)—$N(R^2)(R^2)$, —$S(O)_2$—$N(R^2)(R^2)$, —$N(R^2)$—C(O)—$R^2$, —C(O)—$R^2$, —$S(O)_n(R^2)$, —$OCF_3$, —$S(O)_n$—G, methylenedioxy, —$N(R^2)$—$S(O)_2(R^2)$, halo, —$CF_3$, —$NO_2$, G and —O—G;

$Q_2$ is selected from $D_2$, O—$D_2$, $D_2$—$D_2$, —O—$R^3$, —$NR^2R^3$, alkyl optionally substituted with one or more groups selected from $R^4$ and $D_2$, alkenyl optionally substituted with one or more groups selected from $R^4$ and $D_2$, saturated carbocycle optionally substituted with one or more groups selected from $R^4$ and $D_2$, and unsaturated carbocycle optionally substituted with one or more groups selected from $R^4$ and $D_2$;

each $R^4$ is independently selected from —$OR^2$, —C(O)—$NHR^2$, —$S(O)_2$—$NHR^2$, halo, —$NR^2$—C(O)—$R^2$ and —CN;

$Q_3$ is selected from mercapto, substituted aryl and aryloxyl, and substituted and unsubstituted thioether, amino and partially saturated heterocyle;

$Q_4$–$Q_8$, when present, are each independently selected from hydrogen, hydroxyl, mercapto, nitro, halogen, —O—J wherein J is a substituted or unsubstituted hydrolyzable group, and substituted and unsubstituted alkoxyl, aryloxyl, thioether, acyl, sulfinyl, sulfonyl, amino, alkyl, cycloalkyl, alkenyl, alkynyl, saturated and partially saturated heterocycle and aryl, and further wherein any one or more of $Q_4$–$Q_8$ may be a member of a spiro ring and any two of $Q_4$–$Q_8$ may both be members of a ring;

Y is selected from oxygen, —N—H, —N-alkyl, —N-alkenyl, —N-alkynyl, sulfur, selenium and two hydrogen atoms;

E is carbon or nitrogen; and

A is a carbocycle or heterocycle, and is optionally further substituted;

or a pharmaceutically acceptable salt thereof.

25. A compound of the formula

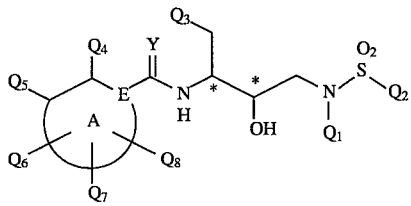

(1)

wherein:

$Q_1$ is selected from substituted and unsubstituted carbocycle, heterocycle, alkyl, alkynyl and alkenyl;

$Q_2$ is selected from hydroxyl, halogen, hydrolyzable group, and substituted and unsubstituted carbocycle, heterocycle, alkyl, alkoxyl, carbocyclyloxyl, heterocyclyloxyl, amino, acyl, alkynyl and alkenyl;

$Q_3$ is selected from mercapto and substituted and unsubstituted alkoxyl, aryloxyl, thioether, amino, alkyl, cycloalkyl, saturated and partially saturated heterocycle, and aryl;

$Q_4$ is methyl;

$Q_5$ is hydroxyl, —O-acetyl or $OPO(OH)_2$;

$Q_6$–$Q_8$, when present, are each independently hydrogen or dioxide;

Y is selected from oxygen, —N—H, —N-alkyl, —N-alkenyl, —N-alkynyl, sulfur, selenium and two hydrogen atoms;

E is carbon; and

A is phenyl;

or a pharmaceutically acceptable salt thereof.

26. A compound or salt of claim 1, which is selected from: N-[(2 syn,3S)-2-hydroxy-4-phenylthio-3-(2'methyl-3'-hydroxyphenyl) carboxamide-butyl]-N-isobutyl-4-methoxy-benzenesulfonamide; N-[(2 syn,3S)-2-hydroxy-4-phenylthio-3-(2'methyl-3'-hydroxyphenyl) carboxamide-butyl]-N-isobutyl-4-hydroxy-benzenesulfonamide; N-cyclopentylmethyl-4-hydroxy-N-((2 syn,3S)-2-hydroxy-4 -phenylthio-3-(2'-methyl-3'-hydroxyphenyl)carboxamide-butyl)benzenesulfonamide; N-cyclopentylmethyl-4-amino-N-((2 syn,3S)-2 -hydroxy-4-phenylthio-3-(2'-methyl-3'-hydroxyphenyl)carboxamide-butyl)-benzenesulfonamide; and N-[(2 syn,3S)-2-hydroxy-4 -phenylthio-3-(2'methyl-3'-hydroxyphenyl)carboxamide-butyl]-N-cyclohexylmethyl- 4-methoxy-benzenesulfonamide.

27. A method of inhibiting HIV protease, comprising administering to a host an effective amount of a compound or salt of claim 26.

28. A pharmaceutical composition comprising an amount of a compound or salt of claim 26 effective to inhibit HIV protease, and a pharmaceutically acceptable carrier.

29. A method of inhibiting HIV protease, comprising administering to a host an effective amount of a compound of the formula (1) as defined in claim 1 or a pharmaceutically acceptable salt thereof.

30. A pharmaceutical composition comprising an amount of a compound of the formula (1) or a pharmaceutically acceptable salt thereof as defined in claim 1 effective to inhibit HIV protease, and a pharmaceutically acceptable carrier.

* * * * *

UNITED STATES PATENT AND TRADEMARK OFFICE
CERTIFICATE OF CORRECTION

PATENT NO. : 5,527,829
DATED : June 18, 1996
INVENTOR(S) : Vincent J. Kalish

It is certified that error appears in the above-identified patent and that said Letters Patent is hereby corrected as shown below:

Column 6, line 19, please change "SO-L$_5$ to --SO$_2$-L$_5$--.

Column 42, line 12, in claim 24, please change "R" to --R$^2$--.

Signed and Sealed this

Thirty-first Day of March, 1998

Attest:

BRUCE LEHMAN

*Attesting Officer*     Commissioner of Patents and Trademarks